(12) United States Patent
Ashida et al.

(10) Patent No.: US 10,405,759 B2
(45) Date of Patent: Sep. 10, 2019

(54) BLOOD PRESSURE MEASUREMENT CUFF AND ATTACHMENT METHOD THEREOF

(71) Applicant: OMRON HEALTHCARE Co., Ltd., Kyoto (JP)

(72) Inventors: Tameo Ashida, Kyoto (JP); Hirotaka Hayashi, Kyoto (JP); Masaki Harada, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 222 days.

(21) Appl. No.: 15/402,707

(22) Filed: Jan. 10, 2017

(65) Prior Publication Data

US 2017/0143217 A1    May 25, 2017

Related U.S. Application Data

(63) Continuation of application No. PCT/JP2015/069490, filed on Jul. 7, 2015.

(30) Foreign Application Priority Data

Jul. 10, 2014   (JP) .................................. 2014-142380

(51) Int. Cl.
*A61B 5/022* (2006.01)
*A61B 5/021* (2006.01)

(52) U.S. Cl.
CPC ...... *A61B 5/02233* (2013.01); *A61B 5/02141* (2013.01); *A61B 5/02208* (2013.01)

(58) Field of Classification Search
CPC ..... A61B 5/021; A61B 5/02141; A61B 5/022; A61B 5/02208; A61B 5/02225; A61B 5/02233
See application file for complete search history.

(56) References Cited

U.S. PATENT DOCUMENTS 4,832,040 A * 5/1989 Ruff ................... A61B 5/02233
                                                      600/499
4,838,276 A * 6/1989 Nagai ................ A61B 5/02233
                                                      600/499
(Continued)

FOREIGN PATENT DOCUMENTS

JP      S55-50340      4/1980
JP      S64-9612 U     1/1989
(Continued)

OTHER PUBLICATIONS

International Search Report issued in corresponding Application No. PCT/JP2015/069490, dated Oct. 13, 2015, (4 pages).

*Primary Examiner* — Todd J Scherbel
(74) *Attorney, Agent, or Firm* — Osha Liang LLP

(57) ABSTRACT

A blood pressure measurement cuff includes a belt-shaped body and a ring having a temporary fastening structure that allows a region continuous with the outer circumferential end of the belt-shaped body to be pulled through the ring away from the measurement site during attachment and suppresses a case in which the region continuous with the outer circumferential end of the belt-shaped body is pulled back through the ring by elastic force of the measurement site. The temporary fastening structure includes a sleeve member fitted around a second side of the ring for pivoting around the second side. The sleeve member includes a first region that allows the outer cloth to slide and a second region having a projection that applies friction to the outer cloth in that order from an upstream side toward a downstream side with respect to a direction in which the belt-shaped body is pulled.

18 Claims, 16 Drawing Sheets

(56) References Cited

U.S. PATENT DOCUMENTS 6,960,223 B1 * 11/2005 Ambach ............ A61B 17/1327
                                                                           606/203
2016/0000342 A1 * 1/2016 Ito ......................... A61B 5/022
                                                                           600/499

FOREIGN PATENT DOCUMENTS

| | | |
|---|---|---|
| JP | H01-75406 U | 5/1989 |
| JP | H05-15283 Y2 | 4/1993 |
| JP | H08-215159 A | 8/1996 |
| JP | 2006-130331 A | 5/2006 |
| WO | 2010/103897 A1 | 9/2010 |
| WO | 2011/108335 A1 | 9/2011 |

* cited by examiner

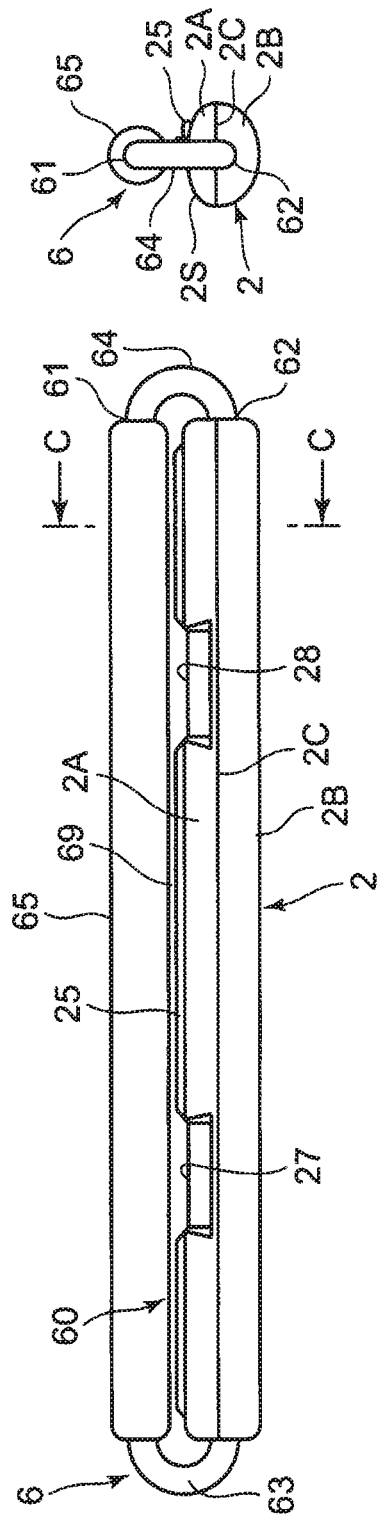
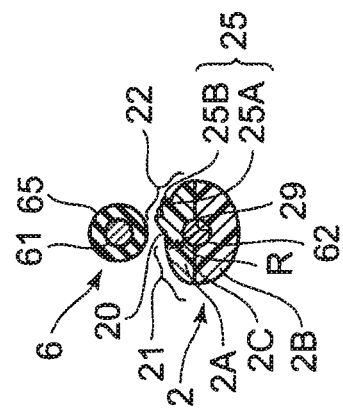
FIG. 3A
FIG. 3B
FIG. 3C

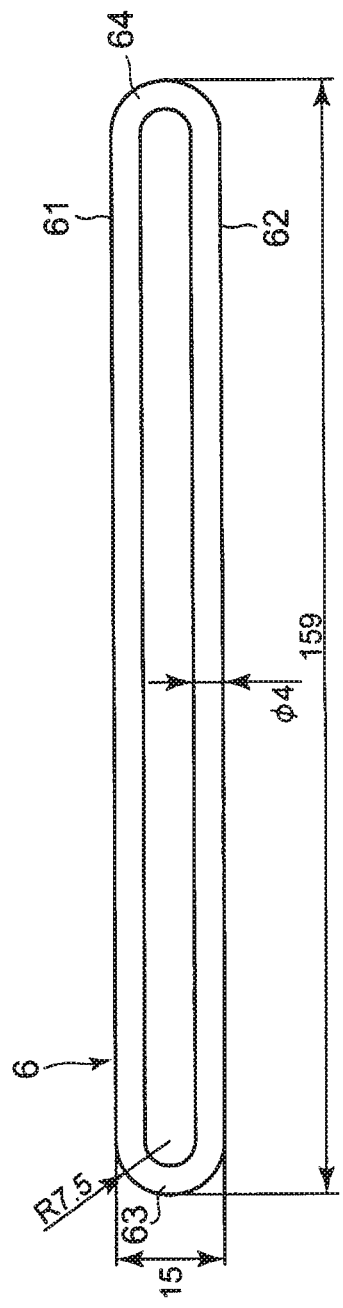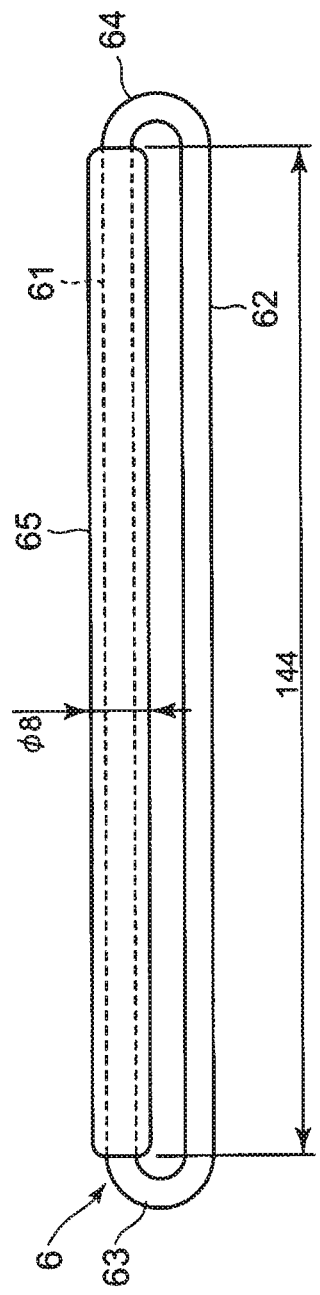

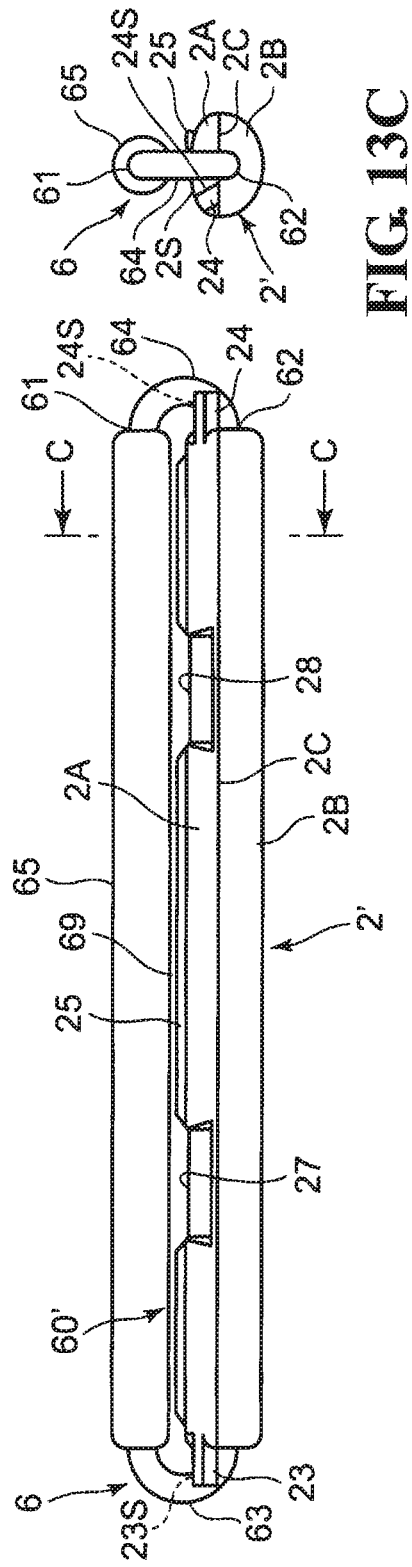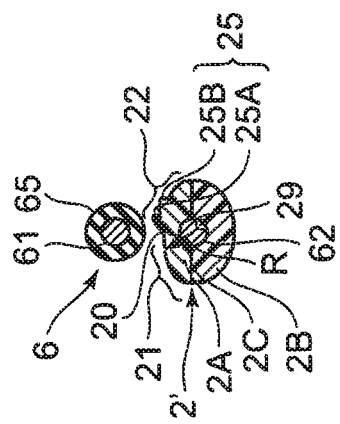

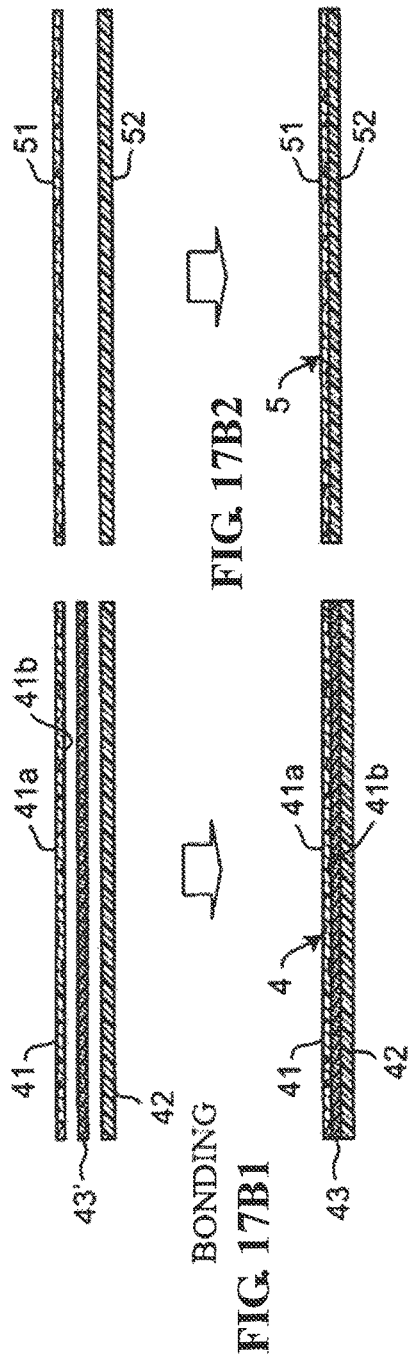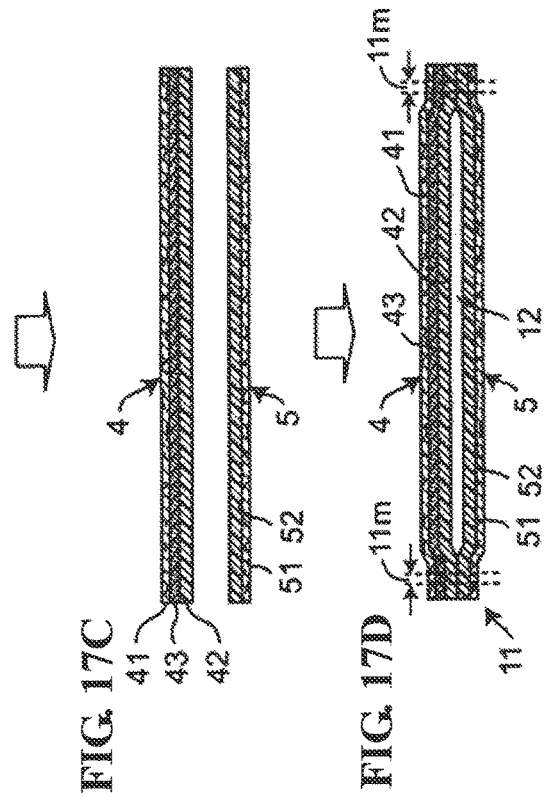

BLOOD PRESSURE MEASUREMENT CUFF AND ATTACHMENT METHOD THEREOF

TECHNICAL FIELD

This invention relates to a blood pressure measurement cuff, and more particularly relates to a cuff that is wrapped around and compresses a measurement site such as a measurement subject's arm or wrist for blood pressure measurement.

Also, this invention relates to a blood pressure measurement cuff attachment method for attaching such a blood pressure measurement cuff to a measurement site.

BACKGROUND ART

Conventionally, as an example of this type of blood pressure measurement cuff, there is known to be a fold-back type of blood pressure measurement cuff (armband), such as that disclosed in Patent Document 1 (JP H08-215159A). As illustrated in FIG. 19A, a cuff 100 includes an oval-shaped fold-back fitting 106 near one end 104e in a length direction of an outer cloth (surface cloth) 104 of the cuff 100, and includes a hook-and-loop fastener (engagement portion) 103 near another end (leading end) 104f in the length direction of the outer cloth 104. An air bladder 102 (see FIG. 18D) is contained between the outer cloth 104 and an inner cloth (underside cloth) 105 of the cuff 100. Also, in this example, a microphone 101 for observing a pulse sound is included at a portion approximately in the center in the length direction.

During attachment, as illustrated in FIG. 19A, the cuff 100 is first made cylindrical by passing the leading end portion 104f through the ring-shaped fold-back fitting 106 with the outer cloth 104 of the cuff facing outward. Next, a left arm 90 serving as a measurement site is passed through the cylindrical cuff from a side at which the cylindrical cuff appears to the measurement subject to be in the form of a clockwise spiral (note that FIGS. 19A and B illustrate cross-sectional views of the left arm 90 as viewed from the measurement subject), and the left arm 90 is adjusted so that the microphone 101 is located almost on an artery 90P when the palm of the hand has been turned upward. Next, the leading end portion 104f is pulled leftward as indicated by arrow A1 so that a gap between the inner cloth 105 of the cuff and the left arm 90 is mostly eliminated. Thereafter, as illustrated in FIG. 19B, a portion continuous with the leading end portion 104f of the cuff is folded back as indicated by arrow B1 from the position of the fold-back fitting 106 and the hook-and-loop fastener 103 is fixed to an opposing portion 104x on the outer cloth 104. Thus, the cuff 100 is attached to the left arm 90 serving as the measurement site. Note that arrow A2 in FIG. 19A and arrow B2 in FIG. 19B each indicate tension acting on the cuff.

In this state, air is pumped into or evacuated from the air bladder 102 through an air tube using a pump, and based on the pulse sound observed using the microphone 101, the blood pressure is measured (Korotkoff method). Note that instead of using the Korotkoff method, the blood pressure can be measured using the oscillometric method (the cuff itself detects change in a pulse wave as a pressure sensor) as well.

CITATION LIST

Patent Literature

Patent Literature 1: JP H08-215159A

SUMMARY OF INVENTION

However, when the measurement subject, for example, attaches the cuff 100 to his or her own left arm 90, he or she positions his or her right hand leftward of the left arm 90 (i.e., lateral to the body) so as to pull the leading end 104f of the cuff 100 leftward (i.e., more laterally from the lateral side of the body) with the right hand as indicated by arrow A1 in FIG. 19A, and is forced to perform an unnatural operation of folding back toward the right as indicated by arrow B1 in FIG. 19B while mostly maintaining the amount of tensile force so that the cuff 100 does not loosen. For this reason, the fold-back type of cuff is problematic in that the measurement subject needs some skill to attach it by himself or herself.

In light of this, the inventors of the present application proposed a novel blood pressure measurement cuff and attachment method thereof (Japanese Patent Application No. 2013-042843).

According to this blood pressure measurement cuff and attachment method thereof, no unnatural operation is required during attachment, unlike the case of using the above-described fold-back type of cuff. This makes it easy for the measurement subject to attached the cuff by himself or herself.

One or more embodiments of the present invention provide an even further improved blood pressure measurement cuff that a measurement subject can easily attach by himself or herself.

Also, one or more embodiments of the present invention provide a blood pressure measurement cuff attachment method according to which a measurement subject can easily attach such a cuff to a measurement site by himself or herself.

The blood pressure measurement cuff according to one or more embodiments of the present invention is a blood pressure measurement cuff to be wrapped in one direction along a circumferential direction around a measurement site, the blood pressure measurement cuff includes:

a belt-shaped body obtained by enveloping a fluid bladder with an inner cloth to be in contact with the measurement site and an outer cloth opposing the inner cloth;

a ring attached via a ring attachment member to a region on an inner circumferential end side of the outer cloth; and a hook-and-loop fastener provided in a region on an outer circumferential end side of the inner cloth and configured to be fixed detachably to the outer cloth, wherein the ring includes a first side that extends in a direction intersecting the circumferential direction, a second side that extends along the first side, and a pair of connecting portions that connect ends of the first and second sides, and at least a portion of the first side is attached to a region on the inner circumferential end side of the outer cloth so as to be surrounded by the ring attachment member, the ring has a temporary fastening structure that allows a region continuous with the outer circumferential end of the belt-shaped body to be pulled through the ring with arm strength away from the measurement site during attachment and suppresses a case in which a region continuous with the outer circumferential end of the belt-shaped body pulled by the arm strength is pulled back through the ring by elastic force of the measurement site;

the temporary fastening structure has a sleeve member fitted around the second side so as to be capable of pivoting;

when the sleeve member is within a range of pivoting around the second side, a gap through which the belt-shaped body can pass is, in a natural state, present between the outer circumferential surface of the ring attachment member and the outer circumferential surface of the sleeve member, and the sleeve member includes, in a range of an outer circumferential surface of the sleeve member that can face the first side, a first region that allows the outer cloth to slide when the region continuous with the outer circumferential end of the belt-shaped body is pulled in a direction away from the measurement site by arm strength and a second region having a projection that, when the region continuous with the outer circumferential end of the belt-shaped body attempts to return through the ring due to elastic force of the measurement site, enters into the as a result of the sleeve member rotating around the second side due to the belt-shaped body and catches on and applies friction to the outer cloth, in that order from an upstream side toward a downstream side with respect to a direction a region of the belt-shaped body continuous with the outer circumferential end is pulled.

In the present specification, "measurement site" refers to a site that can be wrapped by a cuff such as an upper arm or a wrist, in order to measure a measurement subject's blood pressure.

"Wrapping in one direction along the circumferential direction" around the measurement site means wrapping the cuff (belt-shaped body) in the circumferential direction around the measurement site such that it overlaps itself without being folded back. In other words, it means that in a cross-sectional view along the length direction of the measurement site, the cuff (belt-shaped body) is wrapped around the measurement site in a spiral shape.

The belt-shaped body "containing a fluid bladder" means that a substantial portion of a fluid bladder, or in other words, a fluid chamber, is contained in the belt-shaped body. This does not necessarily mean that the entire fluid bladder is completely surrounded by the belt-shaped body. For example, a portion existing on the peripheral edge of the fluid bladder outside of the fluid chamber may be exposed to the outside of the belt-shaped body.

Also, "inner cloth" and "outer cloth" may each be composed of one layer or multiple layers of resin instead of merely being composed of cloths.

"Inner circumferential end" indicates an end on the side that is to be inward when the cuff (belt-shaped body) is wrapped in one direction (spiral shape in cross-sectional view) along the circumferential direction around the measurement site.

"Outer circumferential end" indicates the end on the side that is to be outward when the cuff (belt-shaped body) is wrapped in one direction (spiral shape in cross-sectional view) along the circumferential direction around the measurement site.

The first region "allowing the outer cloth to slide" means that friction applied to the outer cloth by the first region is sufficiently lower than the arm strength pulling the belt-shaped body.

The blood pressure measurement cuff according to one or more embodiments of the present invention is attached to a measurement site (a cuff for wrapping around a left arm is used for convenience in the description) as follows, for example. First, with the outer cloth of the belt-shaped body on the outer side, the measurement subject passes the region of the outer circumferential end side of the belt-shaped body where the hook-and-loop fastener is provided through the ring so as to make the belt-shaped body into a cylinder that is sufficiently wider than the left arm. Next, from the side at which the cylindrical belt-shaped body appears to the measurement subject to be in the form of a counterclockwise spiral (counterclockwise from the inner circumferential end to the outer circumferential end), the left arm is passed through the cylindrical belt-shaped body. Then, adjustment is performed so that the ring is located below or to the right of the measurement site. Next, the measurement subject temporarily pulls the outer circumferential end of the belt-shaped body outward in a radial direction relative to the belt-shaped body (a direction away from the measurement site; in this example, downward or to the right depending on the position of the ring relative to the measurement site) with his or her right hand, substantially eliminating a gap between the inner cloth of the belt-shaped body and the left arm (this operation is referred to as "temporary fastening" where appropriate). At this time, the ring allows the region continuous with the outer circumferential end of the belt-shaped body to be pulled outward in the radial direction (downward or to the right, in this example) through the ring by the arm strength of the right hand. Specifically, for example, it is assumed that at the start of the temporary fastening, the border of the outer circumferential surface of the sleeve member, between the first region and the second region, is near a position opposing the first side (this will be referred to as a "neutral position" where appropriate). From the vicinity of this neutral position, as the region continuous with the outer circumferential end of the belt-shaped body passes through the ring and is pulled from the upstream side toward the downstream side, the sleeve member fitted so as to be capable of pivoting around the second side of the ring rotates around the second side and arrives at an angled position in which the first region of the outer circumferential surface of the sleeve member opposes the first side (this will be referred to as a "first angled position"). As a result, the first region makes contact with the outer cloth of the belt-shaped body and allows the outer cloth of the belt-shaped body to slide. Accordingly, the measurement subject can more easily pull out the region continuous with the outer circumferential end of the belt-shaped body. Meanwhile, the temporary fastening structure of the ring suppresses a case in which the region continuous with the outer circumferential end of the belt-shaped body pulled by the arm strength is pulled back through the ring by the elastic force of the measurement site. Specifically, after the above-described temporary fastening operations, it is assumed that the measurement subject relaxes the tensile force applied by his or her right hand. When the region continuous with the outer circumferential end of the belt-shaped body attempts to return through the ring due to the elastic force of the measurement site, the sleeve member fitted so as to be capable of pivoting around the second side of the ring rotates around the second side with the belt-shaped body in the opposite direction as the pulling direction (this causes the belt-shaped body to slacken slightly; the amount of slackening is referred to as a "set slack amount"), and arrives at an angled position in which the second region of the outer circumferential surface of the sleeve member opposes the first side (this will be referred to as a "second angled position"). As a result, the second region makes contact with the outer cloth of the belt-shaped body and applies friction to the outer cloth of the belt-shaped body. Specifically, the projection of the second region enters into the gap, and catches on and applies friction to the outer cloth of the belt-shaped body. The belt-shaped body slackening more than the set slack amount can thus be suppressed. Thereafter, the measurement subject uses the right hand (e.g., moves the right hand upward on the torso side of the left arm) to, along the circumferential direction of the left arm, align the region continuous with the outer circumferential end of the belt-shaped body with a portion that has not passed through the ring of the belt-shaped body. Accordingly, the hook-and-loop fastener provided in the region on the outer circumferential end side of the inner cloth is fixed to the opposing portion of the outer cloth (this operation will be referred to as "actual fixing" as appropriate). Thus, the cuff is attached in one direction along the circumferential direction to the left arm serving as the measurement site. That is to say, when viewed by the measurement subject along the length direction of the measurement site, it is attached in a counter-clockwise spiral shape.

Note that if the right arm is to be used as the measurement site, it is sufficient that a cuff with a left-right inverted structure is created and the above description of the method for attachment to the left arm is read replacing "left" with "right". Also, if a wrist or the like is to be used as the measurement site, it is sufficient that "upper arm" is replaced with "wrist" or the like (the same follows in the following description).

Thus, the blood pressure measurement cuff does not require an unnatural operation during attachment, unlike the case of the fold-back type of cuff described above. In particular, during the above-described temporary fastening to the left arm, the measurement subject need only temporarily pull the outer circumferential end of the belt-shaped body outward in the radial direction (downward or to the right, in the above example) with the right hand. The operation for temporary fastening is not an operation in which the hand moves further laterally from the lateral side of the body, and there is no need for the measurement subject to continue to use his or her arm strength to maintain the tension of the belt-shaped body until the actual fixing is complete. Accordingly, the measurement subject can easily attach the blood pressure measurement cuff by himself or herself. For example, an obese person whose arm thickness makes it difficult to raise the arm outward from his or her body, an elderly person with little flexibility, or a sick person with little arm strength can perform the attachment easily.

Additionally, in the state of being attached after the actual fixing is complete, the blood pressure measurement cuff is wrapped in one direction along the circumferential direction around the measurement site. That is to say, in the entire region along the circumferential direction of the measurement site, the inner cloth is hidden, and only the outer cloth can be seen on the outside. Usually, in order to compress the measurement site, the inner cloth is set to have a large amount of elasticity, and the outer cloth is set such that it has less elasticity than the inner cloth (or is not elastic). In this case, when air is pumped into the fluid bladder with a pump for blood pressure measurement, with the blood pressure measurement cuff the cloth seen on the front side (outer cloth) does not needlessly inflate outward (to the side opposite to the measurement site). Accordingly, the amount of air supplied to the fluid bladder can be suppressed, resulting in an increase in the efficiency of pressurization.

Also, with the blood pressure measurement cuff, since the cloth seen on the front side (outer cloth) cannot inflate outward needlessly, the measurement subject is not caused to feel uneasy.

Furthermore, with the blood pressure measurement cuff, since the cloth seen on the front side (outer cloth) never needlessly swells outward, an arrangement is possible in which the fluid bladder is extended over most of the region in the circumferential direction (length direction) in the belt-shaped body. With this kind of arrangement, there is no longer a restriction (described below) on the extension range of the air bladder in the circumferential direction in the case of the fold-back type of cuff, and thus the range of dimensions in the circumferential direction of the measurement site set as specifications of the cuff (refers to a range ranging from the minimum circumference to the maximum circumference; the same applies hereinafter) can be widened.

Also, it is known that the compression force compressing the artery of the measurement site depends on the dimension in the circumferential direction of the fluid bladder and the dimension in the width direction that intersects the circumferential direction. The larger the dimension in the circumferential direction and the dimension in the width direction of the fluid bladder are, the larger the compression force is. Here, according to the arrangement in which the fluid bladder is extended over most of the region in the circumferential direction, the dimension in the width direction of the fluid bladder can be reduced instead in order to obtain the needed compression force. If the dimension in the width direction of the fluid bladder is thus reduced, and the dimension in the width direction of the belt-shaped body is accordingly reduced, the measurement subject can more easily attach the blood pressure measurement cuff. Also, if the dimensions in the width direction of the fluid bladder and the belt-shaped body are reduced, the cost of materials can be reduced. Accordingly, the blood pressure measurement cuff can be produced at a low cost.

When the measurement subject is to remove the cuff from the left arm, first, the hook-and-loop fastener provided on the region on the outer circumferential end side of the inner cloth is separated from the opposing portion of the outer cloth with the right hand (actual fixing removal). Next, for example, the measurement subject inserts a finger of his or her right hand between the belt-shaped body and the left arm and applies a pressure greater than the friction applied by the second region of the sleeve member, so that the cylinder diameter of the belt-shaped body widens. Upon doing so, the region continuous with the outer circumferential end of the belt-shaped body is pulled back through the ring while receiving the friction from the second region. Accordingly, the belt-shaped body becomes a cylinder that is sufficiently wider than the left arm (temporary fastening removal). Thereafter, the cuff is removed from the left arm.

Note that with the fold-back type of cuff, due to the fact that the inner cloth can be seen on the front side in the folded-back region near the leading end, if the air bladder were to be extended to the folded-back region, the cloth seen on the front side (inner cloth) would inflate outward (to the side opposite to the measurement site) needlessly when air is pumped into the air bladder with a pump for blood pressure measurement. For this reason, the amount of air supplied to the air bladder would increase, resulting in a reduction in the efficiency of pressurization. Also, the measurement subject would feel uneasy about the expansion being abnormal. Accordingly, with the fold-back type of cuff, there is an actual problem in that the air bladder cannot be extended beyond the fold-back fitting in the circumferential direction. Because of the restriction on the extension range in the circumferential direction of the air bladder, the range of dimensions in the circumferential direction of the measurement site set as specifications of the cuff is narrower. More specifically, since the air bladder cannot be extended to the folded-back region, the minimum circumference cannot be less than the dimension in the circumferential direction of the air bladder. Also, since the dimension in the circumferential direction of the air bladder is reduced such that it is smaller than the dimension in the circumferential direction of the belt-shaped body, the maximum circumference is restricted to a dimension that is relatively small (it is thought that the dimension in the circumferential direction of the air bladder usually needs to be about two-thirds or more of the maximum circumference applied to the cuff). Also, in order to obtain the needed compression force, the dimension in the width direction of the air bladder cannot be reduced, and the dimension in the width direction of the belt-shaped body also cannot be accordingly reduced.

Also, cuffs of a type that wrap in one direction along the circumferential direction around a measurement site and do not have the above-described ring or temporary fastening structure are widely used as cuffs for medical institutions. However, it is envisioned that such cuffs for medical institutions are attached to a measurement site of a patient (measurement subject) by a medical professional (doctor, nurse, or the like) using both hands, and it is difficult for a measurement subject to attach it by himself or herself.

A blood pressure measurement cuff according to an embodiment further includes a restricting element that restricts a range in which the sleeve member can pivot around the second side to a range from a first angled position, at which the first region of the outer circumferential surface of the sleeve member opposes the first side, to a second angled position, at which the second region opposes the first side.

In the blood pressure measurement cuff according to this embodiment, the restricting element restricts the range in which the sleeve member can pivot around the second side to a range from the first angled position, at which the first region of the outer circumferential surface of the sleeve member opposes the first side, to the second angled position, at which the second region opposes the first side. Accordingly, when the region continuous with the outer circumferential end of the belt-shaped body is pulled through the ring as a result of the above-described temporary fastening operations, the sleeve member will stop at the first angled position even when the sleeve member rotates around the second side due to the belt-shaped body. As a result, the first region reliably makes contact with the outer cloth of the belt-shaped body and reliably allows the outer cloth of the belt-shaped body to slide. Accordingly, the measurement subject can more easily pull out the region continuous with the outer circumferential end of the belt-shaped body. Additionally, when the measurement subject relaxes the tensile force applied by the right hand after the above-described temporary fastening operations and the region continuous with the outer circumferential end of the belt-shaped body attempts to return through the ring, even if the sleeve member rotates around the second side due to the belt-shaped body in the opposite direction as the direction of the pulling, the sleeve member will stop at the aforementioned second angled position. As a result, the second region reliably makes contact with the outer cloth of the belt-shaped body and reliably applies friction to the outer cloth of the belt-shaped body. The belt-shaped body slackening more than the set slack amount can thus be reliably suppressed.

With a blood pressure measurement cuff according to an embodiment, the restricting element includes the outer circumferential surface of the sleeve member as a first restricting element; and a radius of a cross-section of the sleeve member perpendicular to the second side increases gradually around the sleeve member with distance from a border between the first region and the second region, and when the sleeve member rotates around the second side with the region continuous with the outer circumferential end of the belt-shaped body passed through the ring, the outer circumferential surface of the sleeve member makes contact and engages with the outer cloth of the belt-shaped body passing through the ring.

With the blood pressure measurement cuff according to this embodiment, when the sleeve member rotates around the second side with the region continuous with the outer circumferential end of the belt-shaped body passed through the ring, the outer circumferential surface of the sleeve member makes contact and engages with the outer cloth of the belt-shaped body passing through the ring. Thus as described above, the range in which the sleeve member can pivot around the second side is restricted to the range from the first angled position, at which the first region of the outer circumferential surface of the sleeve member opposes the first side, to the second angled position, at which the second region opposes the first side. Accordingly, the measurement subject can more easily pull out the region continuous with the outer circumferential end of the belt-shaped body during the above-described temporary fastening operations. Additionally, the second region reliably makes contact with the outer cloth of the belt-shaped body and reliably applies friction to the outer cloth of the belt-shaped body after the above-described temporary fastening operations. The belt-shaped body slackening more than the set slack amount can thus be reliably suppressed.

With a blood pressure measurement cuff according to an embodiment, the restricting element includes, as a second restriction element, a pin projecting from an end surface of the sleeve member in the length direction thereof and disposed in a predetermined location corresponding to the first region around the center of the sleeve member, and the pin makes contact and engages with the connecting portion of the ring when the sleeve member rotates around the second side, and as a result, the first angled position is restricted to an angled position closer to a neutral position, at which the border between the first region and the second region of the outer circumferential surface of the sleeve member opposes the first side, than an angled position determined by the outer circumferential surface of the sleeve member serving as the first restricting element.

In the case where, particularly at the first region of the outer circumferential surface of the sleeve member, the radius of a cross-section perpendicular to the second side increases gradually around the sleeve member with distance from a border between the first region and the second region, when as a result of the above-described temporary fastening operations, the sleeve member rotates around the second side as the region continuous with the outer circumferential end of the belt-shaped body is pulled out, it is possible that the belt-shaped body will become caught in a gap between the outer circumferential surface of the sleeve member and the outer circumferential surface of the ring attachment member and receive friction that cannot be ignored. Here, with the blood pressure measurement cuff according to this embodiment, the restricting element includes, as the second restriction element, a pin projecting from an end surface of the sleeve member in the length direction thereof and disposed in a predetermined location corresponding to the first region around the center of the sleeve member. The pin makes contact and engages with the connecting portion of the ring when the sleeve member rotates around the second side, and as a result, the first angled position is restricted to an angled position closer to a neutral position (that is, a position at which the border between the first region and the second region of the outer circumferential surface of the sleeve member opposes the first side) than an angled position determined by the outer circumferential surface of the sleeve member serving as the first restricting element. Accordingly, the gap can be secured between the outer circumferential surface of the sleeve member and the outer circumferential surface of the ring attachment member, and a situation in which the belt-shaped body is caught in the gap between the outer circumferential surface of the sleeve member and the outer circumferential surface of the ring attachment member can be avoided. As a result, the measurement subject can more easily pull out the region continuous with the outer circumferential end of the belt-shaped body through the ring.

Additionally, with the blood pressure measurement cuff according to this embodiment, the first angled position is an angled position closer to the neutral position, and thus the above-described set slack amount (that is, slack in the belt-shaped body resulting from the sleeve member rotating around the second side from the first angled position to the second angled position after the temporary fastening operations) can be reduced. Slackening in the belt-shaped body between the above-described temporary fastening operations and the actual fixing can therefore be further suppressed.

With a blood pressure measurement cuff according to an embodiment, the projection suppresses a state in which the belt-shaped body slackens beyond a predetermined set amount (a set slack amount).

With the blood pressure measurement cuff according to this embodiment, when the sleeve member rotates around the second side in the opposite direction as the direction of the pulling due to the belt-shaped body and arrives at the second angled position after the above-described temporary fastening operations, the belt-shaped body slackening more than the set slack amount can be reliably suppressed.

With a blood pressure measurement cuff according to an embodiment, when viewed along the length direction of the sleeve member, a tip of the projection in the second region projects at an angle away from the border between the first region and the second region, around the circumference of the sleeve member.

With the blood pressure measurement cuff according to this embodiment, when viewed along the length direction of the sleeve member, a tip of the projection in the second region projects at an angle away from the border between the first region and the second region, around the circumference of the sleeve member. Accordingly, when the sleeve member rotates around the second side in the opposite direction as the direction of the pulling due to the belt-shaped body and arrives at the second angled position after the above-described temporary fastening operations, the tip of the projection reliably catches on and applies a large amount of friction to the outer cloth of the belt-shaped body. The belt-shaped body slackening more than the set slack amount can thus be reliably suppressed.

With a blood pressure measurement cuff according to an embodiment, a plurality of the projections of the second region are provided and are arranged along the circumference of the sleeve member.

With the blood pressure measurement cuff according to this embodiment, a plurality of the projections of the second region are provided and are arranged along the circumference of the sleeve member. Accordingly, when the sleeve member rotates around the second side in the opposite direction as the direction of the pulling due to the belt-shaped body after the above-described temporary fastening operations, one of the plurality of projections catches on and applies friction to the outer cloth of the belt-shaped body. The belt-shaped body slackening more than the set slack amount can thus be reliably suppressed.

With a blood pressure measurement cuff according to an embodiment, an expanded portion extending along the length direction is provided around the first side, and the expanded portion is wrapped by the ring attachment member.

With the blood pressure measurement cuff according to this embodiment, an expanded portion extending along the length direction is provided around the first side, and the expanded portion is wrapped by the ring attachment member. Accordingly, it is easy to set a dimension of the gap between the outer circumferential surface of the sleeve member and the outer circumferential surface of the ring attachment member (a closest distance) in accordance with the thickness of the expanded portion in the radial direction. This makes it easy to use the same type of fold-back fitting as is used in conventional fold-back type cuffs to configure the ring itself. In such a case, it is easy to increase the mechanical strength of the ring, as compared to a case where a plastic material is used.

Note that the dimension of the gap is set to be slightly greater than the thickness of the belt-shaped body. This is because first, when the sleeve member is close to the neutral position, the region continuous with the outer circumferential end of the belt-shaped body can be pulled through the gap smoothly, and second, when the region continuous with the outer circumferential end of the belt-shaped body attempts to return through the ring after the above-described temporary fastening operations, the projection of the second region of the sleeve member can enter into the gap, and catch on and apply friction to the outer cloth of the belt-shaped body. In the specification, the "thickness" of the belt-shaped body refers to the thickness of the belt-shaped body itself, excluding the hook-and-loop fastener and the like. Also, if the thickness varies depending on the region of the belt-shaped body, it refers to the maximum thickness.

In addition, with the blood pressure measurement cuff according to this embodiment, a curvature factor of the outer circumferential surface of the ring attachment member is lower than in a case where the expanded portion is not provided. As a result, the distance between the outer circumferential surface of the sleeve member and the outer circumferential surface of the ring attachment member in the direction in which the region continuous with the outer circumferential end of the belt-shaped body passes changes little. Accordingly, when the sleeve member rotates around the second side in the opposite direction as the direction of the pulling due to the belt-shaped body and arrives at the second angled position after the above-described temporary fastening operations, the range in which the projection of the second region of the outer circumferential surface of the sleeve member can make contact with the outer cloth of the belt-shaped body is widened in the direction in which the region continuous with the outer circumferential end of the belt-shaped body passes, and the friction is reliably applied to the outer cloth of the belt-shaped body. The belt-shaped body slackening more than the set slack amount can thus be reliably suppressed.

With a blood pressure measurement cuff according to an embodiment, the expanded portion is made from an elastic material.

With the blood pressure measurement cuff according to this embodiment, the expanded portion is made from an elastic material. Accordingly, when the sleeve member rotates around the second side in the opposite direction as the direction of the pulling due to the belt-shaped body and arrives at the second angled position after the above-described temporary fastening operations, the second region of the outer circumferential surface of the sleeve member enters a state of contact with the outer cloth of the belt-shaped body, and the sleeve member receives a compressive force from the projection of the second region via the belt-shaped body and the ring attachment member, which reduces the curvature factor of the outer circumferential surface of the expanded portion. Accordingly, the range in which the projection of the second region of the outer circumferential surface of the sleeve member can make contact with the outer cloth of the belt-shaped body is widened in the direction in which the region continuous with the outer circumferential end of the belt-shaped body passes, and the friction is reliably applied to the outer cloth of the belt-shaped body. The belt-shaped body slackening more than the set slack amount can thus be more reliably suppressed.

With a blood pressure measurement cuff according to an embodiment, an indentation allowing a fluid within the fluid bladder to flow in the circumferential direction is provided on a side of the outer circumferential surface of the sleeve member around the second side that opposes the first side, in a specific location with respect to the length direction.

With the blood pressure measurement cuff according to this embodiment, an indentation allowing a fluid within the fluid bladder to flow in the circumferential direction is provided in the outer circumferential surface of the expanded portion around the first side or on a side of the outer circumferential surface of the sleeve member around the second side that opposes the first side, in a specific location with respect to the length direction. Accordingly, when an arrangement is employed in which the fluid bladder is extended over most of the region in the circumferential direction (length direction) in the belt-shaped body as described above, the indentation allows the fluid in the fluid bladder to flow in the circumferential direction. Thus the fluid can be supplied and evacuated smoothly across the entirety of the fluid bladder in the circumferential direction. Blood pressure measurements can be taken smoothly using the blood pressure measurement cuff as a result.

Meanwhile, in the case where the expanded portion is provided around the first side, it is desirable that a ring-shaped indentation following the outer circumference of the expanded portion be provided in a specific location with respect to the length direction of the expanded portion so as to allow the flow of the fluid within the fluid bladder in the circumferential direction. In this case, it is desirable that a cutout be provided in a region of the ring attachment member corresponding to the indentation in the expanded portion. As a result, the fluid can be supplied and evacuated smoothly across the entirety of the fluid bladder in the circumferential direction. Blood pressure measurements can be taken smoothly using the blood pressure measurement cuff as a result.

With a blood pressure measurement cuff according to an embodiment, the thickness of the belt-shaped body is substantially uniform.

In the specification, as described above, the "thickness" of the belt-shaped body refers to the thickness of the belt-shaped body itself, excluding the hook-and-loop fastener and the like.

With the blood pressure measurement cuff according to this embodiment, the thickness of the belt-shaped body is substantially uniform, and thus at the time of the above-described temporary fastening, the measurement subject can easily pull the region continuous with the outer circumferential end of the belt-shaped body through the gap between the outer circumferential surface of the sleeve member and the outer circumferential surface of the ring attachment member.

Note that it is desirable that the region of the belt-shaped body (the inner cloth) where the hook-and-loop fastener is provided (a region where the cuff as a whole is thicker than the belt-shaped body itself by an amount equivalent to the thickness of the hook-and-loop fastener) already be passed through the ring when the cuff is shipped.

On the other hand, with the blood pressure measurement cuff according to this embodiment, after the above-described temporary fastening to the left arm, when the measurement subject reduces the tensile force of the right hand, the temporary fastening structure of the ring can suppress a case in which the region continuous with the outer circumferential end of the belt-shaped body is pulled back through the ring, regardless of whether or not any portion of the belt-shaped body is located in the ring, or in other words, regardless of the dimension in the circumferential direction of the measurement site.

With a blood pressure measurement cuff according to an embodiment, the outer cloth of the belt-shaped body has raised fibers, and the raised fibers are down-grain with respect to the direction in which the region continuous with the outer circumferential end is pulled through the ring.

With the blood pressure measurement cuff according to the embodiment, the outer cloth of the belt-shaped body has raised fibers, and the raised fibers are down-grain with respect to the direction in which the region continuous with the outer circumferential end is pulled through the ring. Accordingly, during the operations of temporary fastening to the left arm described above, the region continuous with the outer circumferential end of the outer cloth of the belt-shaped body slides smoothly upon the first region of the sleeve member around the second side. Accordingly, the region continuous with the outer circumferential end of the belt-shaped body is easily pulled through the ring. On the other hand, the raised fibers of the outer cloth are up-grain when the measurement subject relaxes the tensile force on the belt-shaped body and the region continuous with the outer circumferential end of the belt-shaped body attempts to return through the ring after the above-described temporary fastening operations. The projection of the second region of the sleeve member thus applies an even greater amount of friction to the outer cloth of the belt-shaped body. Slackening in the belt-shaped body can thus be more reliably suppressed.

With a blood pressure measurement cuff according to an embodiment, the region of the outer circumferential end side of the belt-shaped body where the hook-and-loop fastener is provided is in a state of being passed through the ring, and the belt-shaped body has a substantially ring shape as a result.

Here, "substantially ring-shaped" means that there is a portion where the belt-shaped body is in a ring shape. For example, the outer circumferential end of the belt-shaped body that has passed the ring may be outside of the ring-shape. Additionally, "ring-shaped" need not refer to a three-dimensional state, and may be a flat state, a folded-over state, or the like.

With the blood pressure measurement cuff according to this embodiment, the region of the outer circumferential end side of the belt-shaped body where the hook-and-loop fastener is provided (the region where the cuff as a whole is thicker than the belt-shaped body itself by an amount equivalent to the thickness of the hook-and-loop fastener) is in a state of being passed through the ring, and the belt-shaped body has a substantially ring shape as a result. Accordingly, when using the cuff, a user does not need to pass the outer circumferential end of the belt-shaped body through the ring to the region where the hook-and-loop fastener is provided, which eliminates that burden. Conversely, the hook-and-loop fastener serves as a stopper and makes it difficult for the outer circumferential end of the belt-shaped body to pull out from the ring.

A blood pressure measurement cuff attachment method according to one or more embodiments of the present invention is a blood pressure measurement cuff attachment method for attaching any of the above-described blood pressure measurement cuffs such that a measurement site is wrapped in one direction along a circumferential direction, the method including:

an arrangement step of, with the outer cloth of the belt-shaped body on the outer side, passing the region of the outer circumferential end side of the belt-shaped body where the hook-and-loop fastener is provided through the ring so as to make the belt-shaped body into a cylinder that is wider than the measurement site, and, from a side at which the cylindrical cuff appears to a measurement subject to be in the form of a counterclockwise spiral when the measurement site is located on a left body half of the measurement subject, passing the measurement site through the cylindrical belt-shaped body and adjusting the belt-shaped body so that the ring is below or to the right of the measurement site, or from a side at which the cylindrical cuff appears to the measurement subject to be in the form of a clockwise spiral when the measurement site is located on a right body half of the measurement subject, passing the measurement site through the cylindrical belt-shaped body and adjusting the belt-shaped body so that the ring is below or to the left of the measurement site;

a temporary fastening step of pulling an outer circumferential end of the belt-shaped body outward in a radial direction relative to the cylinder formed by the belt-shaped body with a hand belonging to a body half opposite to a body half to which the measurement site belongs, so as to substantially eliminate a gap between the inner cloth of the belt-shaped body and the measurement site, wherein the ring allows the region continuous with the outer circumferential end of the belt-shaped body to be pulled outward in the radial direction by the arm strength of the hand through the ring, whereas the temporary fastening structure of the ring suppresses a case in which the region continuous with the outer circumferential end of the belt-shaped body pulled by the arm strength is pulled back through the ring by elastic force of the measurement site; and an actual fixing step of bringing the region continuous with the outer circumferential end of the belt-shaped body along the circumferential direction of the measurement site into alignment with an orientation that is the same as that of a portion that has not passed through the ring of the belt-shaped body, so as to fix the hook-and-loop fastener provided on the region on the outer circumferential end side of the inner cloth to an opposing portion on the outer cloth.

In the blood pressure measurement cuff attachment method according to one or more embodiments of the present invention, no unnatural operation is required during attachment, unlike the case of using the above-described fold-back type of cuff. In particular, in the above-described temporary fastening step, the measurement subject need only temporarily pull the outer circumferential end of the belt-shaped body outward in the radial direction (a direction away from the measurement site) with his or her hand. The operation for temporary fastening is not an operation in which the hand moves in a direction heading further to the side away from the body, and there is no need for the measurement subject to continue to use his or her arm strength to maintain the tensile force of the belt-shaped body until the actual fixing step is complete. Accordingly, according to the blood pressure measurement cuff attachment method of one or more embodiments of the present invention, the measurement subject can easily attach the cuff to a measurement site by himself or herself. For example, an obese person whose arm thickness makes it difficult to raise the arm outward from his or her body, an elderly person with little flexibility, or a sick person with little arm strength can easily perform the attachment bu himself or herself.

Advantageous Effects of Invention

As is evident from the above description, a measurement subject can easily attach the blood pressure measurement cuff according to one or more embodiments of the present invention by himself or herself.

BRIEF DESCRIPTION OF DRAWINGS

FIG. 3A is a diagram illustrating a ring of the cuff having a temporary fastening structure, seen from approximately the same side as in FIG. 2. FIG. 3B is a diagram illustrating the ring shown in FIG. 3A from the right side. FIG. 3C is a diagram illustrating a cross-section taken along line C-C in FIG. 3A.

FIG. 4A is a diagram illustrating the ring itself. FIG. 4B is a diagram illustrating a state in which the ring is provided with an expanded portion.

FIG. 13A is a diagram illustrating a ring of the cuff having a temporary fastening structure according to a variation, seen from approximately the same side as in FIG. 2. FIG.

13B is a diagram illustrating the ring shown in FIG. 13A from the right side. FIG. 13C is a diagram illustrating a cross-section taken along line C-C in FIG. 13A.

FIGS. 17A1 and 17A2 to 17D are process diagrams illustrating a method of manufacturing the cuff.

DESCRIPTION OF EMBODIMENTS

Hereinafter, an embodiment of the present invention will be described in detail with reference to the drawings.

Figure 1:
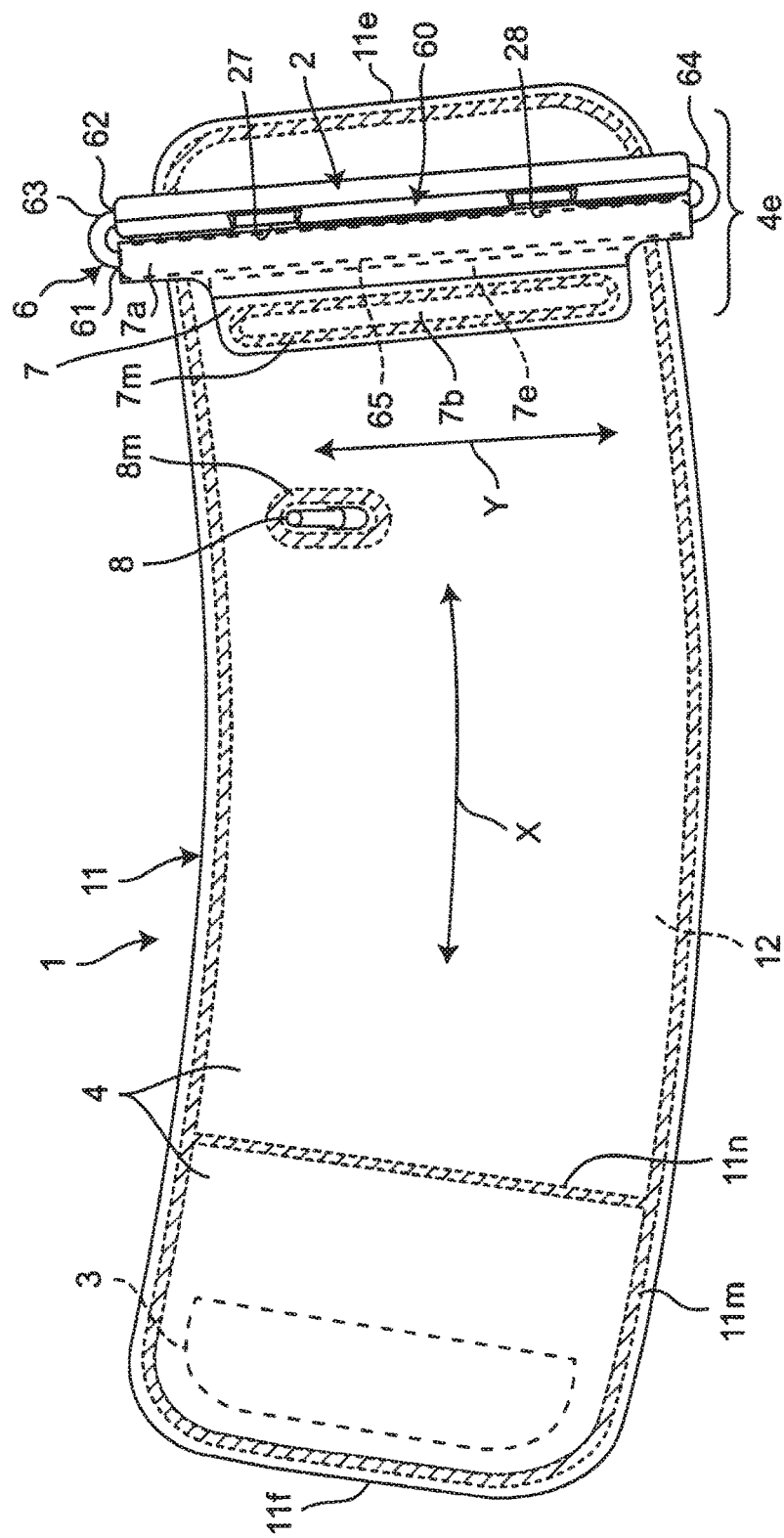
FIG. 1 is a plan view illustrating a blood pressure measurement cuff according to an embodiment of the present invention in an expanded state, seen from an outer cloth side.
Figure 2:
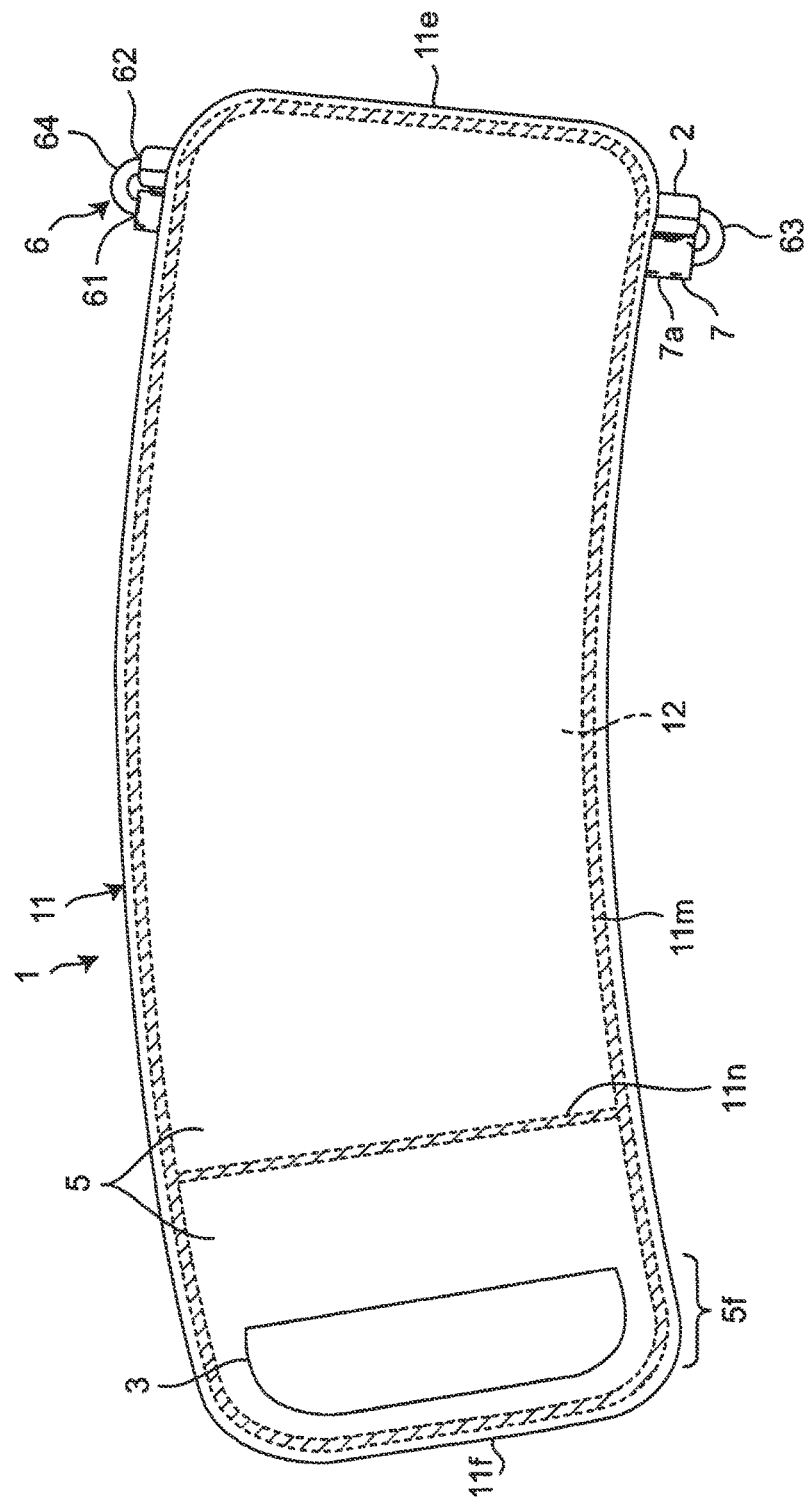
FIG. 2 is a plan view illustrating the cuff in an expanded state, seen from an inner cloth side.

FIGS. 1 and 2 illustrate a blood pressure measurement cuff according to an embodiment of this invention (denoted overall by reference numeral 1) in an expanded state, seen from an outer cloth 4 side and an inner cloth 5 side, respectively. The cuff 1 is to be wrapped in one direction along the circumferential direction around a measurement site (e.g., the left arm).

The cuff 1 includes an elongated belt-shaped body 11 that extends in a substantially circular arc shape. In a state of being attached to the measurement site, a direction X in which in the belt-shaped body 11 extends is substantially the same as the circumferential direction of the measurement site (for this reason, the circumferential direction of the measurement site is indicated by the same reference numeral X where appropriate).

Figure 6:
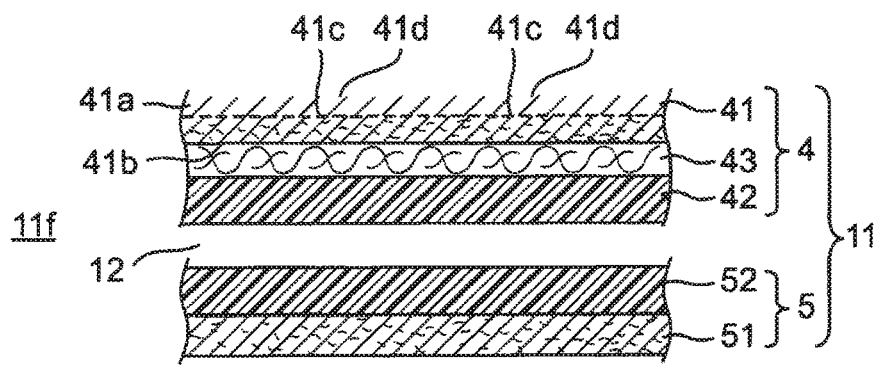
FIG. 6 is a diagram illustrating a cross-sectional structure of a belt-shaped body that forms the cuff.

The belt-shaped body 11 includes an inner cloth 5 (illustrated in FIG. 2) that is to be in contact with the measurement site, and an outer cloth 4 (illustrated in FIG. 1) that opposes the inner cloth 5. The peripheral edges of the inner cloth 5 and the outer cloth 4 are welded together along a ring-shaped line 11m so as to form a bag shape (welded regions are denoted by diagonal lines). In this example, the inner cloth 5 is made from polyester cloth 51 woven with a high degree of elasticity for the purpose of compressing the measurement site, and a polyurethane film 52 bonded to a back side of the polyester cloth 51, as illustrated in FIG. 6. The outer cloth 4 is made from nylon cloth 41 woven from nylon fibers, a tarpaulin layer (containing polyvinyl chloride (PVC) for bonding purposes in the gaps between threads) 43, bonded to a back side of the nylon cloth 41, that is coarser than the nylon cloth 41 and is woven so as to be substantially non-elastic, and a polyurethane film 42 bonded to a back side of the tarpaulin layer 43. The nylon cloth 41 includes a knitted fabric 41b and raised fibers 41a provided on a front side of the knitted fabric 41b. The raised fibers 41a are formed in a loop shape so as to engage with a later-described hook-and-loop fastener (hook) 3. In a view from an outer circumferential end 11f, which will be described next, the raised fibers 41a are down-grain (peaks 41d of the loops fall away from the outer circumferential end 11f with respect to bases 41c of the loops).

As illustrated in FIGS. 1 and 2, the belt-shaped body 11 has an inner circumferential end 11e on the side that is to be inward and an outer circumferential end 11f on the side that is to be outward when wrapped in one direction (a spiral shape in a cross-sectional view along the length direction of the measurement site) along the circumferential direction around the measurement site. At a location near the outer circumferential end 11f of the belt-shaped body 11, the inner cloth 5 and the outer cloth 4 are welded together along a division line 11n that extends in a width direction Y that is perpendicular to the extension direction X. Accordingly, an air bladder 12 serving as a fluid bladder is partitioned by the division line 11n and the ring-shaped line 11m on the right side of the division line 11n in FIGS. 1 and 2, between the inner cloth 5 and the outer cloth 4. As a result, the thickness of the belt-shaped body 11 is substantially uniform.

A hook-and-loop fastener 3 is provided in a region 5f on the outer circumferential end 11f side of the inner cloth 5. The hook-and-loop fastener 3 has hook-shaped raised fibers (not shown) and can be detachably fixed to the outer cloth 4 (the raised fibers 41a thereof).

A ring 6 having a temporary fastening structure 60 is attached via a ring attachment member 7 in a region 4e at the inner circumferential end 11e side of the outer cloth 4. Although the ring 6 is attached so as to follow the width direction Y of the belt-shaped body 11 in this example, the ring 6 may be attached at a slight angle relative to the width direction Y.

FIG. 3A illustrates the ring 6 that has the temporary fastening structure 60, seen from approximately the same side as in FIG. 2. FIG. 3B illustrates the ring 6 shown in FIG. 3A from the right side. FIG. 3C illustrates a cross-section taken along line C-C in FIG. 3A. The ring 6 having the temporary fastening structure 60 is constituted by taking the oval-shaped ring 6, which is the same type of fold-back fitting as is used in the conventional fold-back type cuff 100, and attaching an expanded portion 65 and a sleeve member 2 thereto.

As illustrated in FIG. 4A, the ring 6 itself is made from a metal material formed as a single entity, and includes a rod-shaped first side 61 extending along the width direction Y of the belt-shaped body 11, a rod-shaped second side 62 extending along the first side 61, and a pair of circular arc-shaped connecting portions 63 and 64 that connect end portions of the first and second sides 61 and 62 to each other. In this example, the diameters of the first and second sides 61 and 62 are both set to 4 mm, and the outer diameters of the circular arcs of the connecting portions 63 and 64 are both set to 7.5 mm. The overall length of the ring 6 is set to 159 mm. Because the same type of fold-back fitting as those already in use is employed as the ring 6, it is easy to give the ring 6 greater mechanical strength than in a case where a plastic material is used.

As illustrated in FIG. 4B, the expanded portion 65, which extends along the length direction, is provided around the first side 61 of the ring 6. This expanded portion 65 is made from an elastomer, serving as an elastic material, and is provided integrally with the first side 61. In this example, the length of the expanded portion 65 is set to 144 mm and the outer diameter of the expanded portion 65 is set to 8 mm. As illustrated in FIG. 1, the ring attachment member 7 surrounds the expanded portion 65 when the cuff 1 is in a completed state.

Figure 5D:
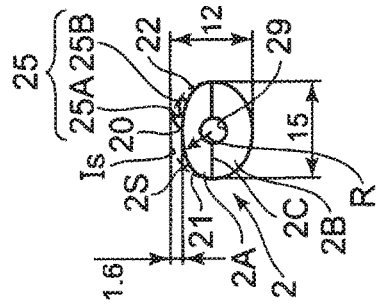
FIG. 5D is a diagram illustrating the sleeve member shown in FIG. 5B from the right side.
Figure 5A:
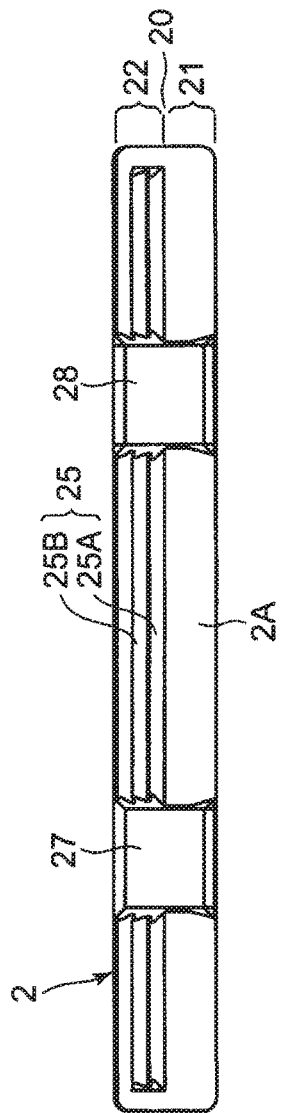
FIG. 5A is a diagram illustrating the sleeve member shown in FIG. 5B from above.
Figure 5B:
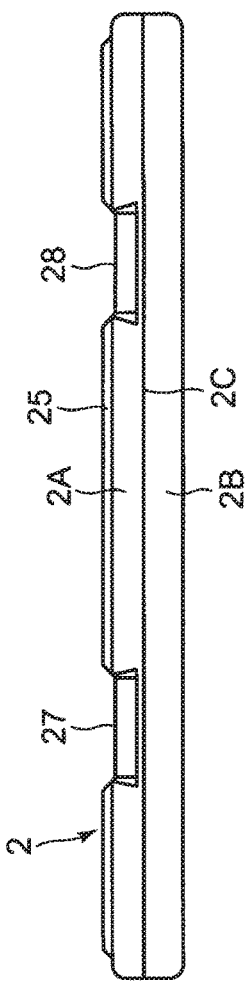
FIG. 5B is a diagram illustrating a sleeve member shown in FIG. 3A alone.
Figure 5C:
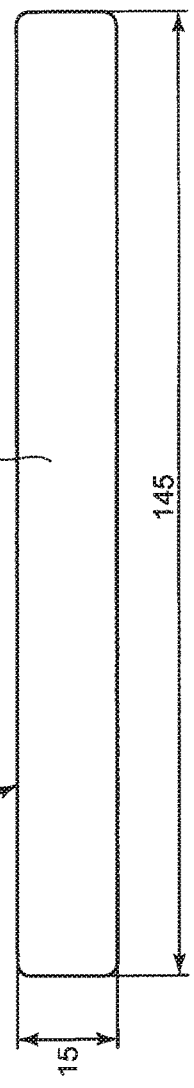
FIG. 5C is a diagram illustrating the sleeve member shown in FIG. 5B from below.

FIG. 5B illustrates the sleeve member 2 shown in FIG. 3A alone, whereas FIGS. 5A, 5C, and 5D illustrate the sleeve member 2 shown in FIG. 5B from above, below, and the right side, respectively. As illustrated in FIG. 5C, the length of the sleeve member 2 in the length direction is set to 145 mm and the width is set to 15 mm.

As illustrated in FIGS. 5B and 5D, the sleeve member 2 is made from a plastic material (ABS resin (acrylonitrile butadiene styrene copolymer), for example), and is divided into an upper portion 2A and a lower portion 2B by a divided surface 2C (note that "upper portion" and "lower portion" are terms used simply to facilitate the descriptions).

As illustrated in FIG. 5D, the sleeve member 2 has a generally elliptical cross-section. The profile of the lower portion 2B follows an ellipse Is whose major axis length is 15 mm and whose minor axis length is 12 mm. The profile of the upper portion 2A follows an ellipse that is flatter than the ellipse Is, that is, an ellipse whose major axis length is 15 mm and whose minor axis length is shorter than the minor axis length of the ellipse Is by 1.6 mm on one side thereof. A hole 29 for fitting with the second side 62 is formed in a location of the sleeve member 2 corresponding to the center of the ellipse Is. An inner diameter dimension of the hole 29 is set to approximately 4 mm, which is approximately the same as the outer diameter dimension of the second side 62 of the ring 6 (to be more precise, the inner diameter dimension of the hole 29 is set to be slightly larger than the outer diameter dimension of the second side 62 of the ring 6 to allow the sleeve member 2 to pivot).

As illustrated in FIGS. 5A and 5D, a first region 21 that allows the outer cloth 4 to slide and a second region 22 that applies friction to the outer cloth 4 are provided, in a range of an outer circumferential surface 2S of the sleeve member 2 that can face the first side 61 (the upper portion 2A), in that order from an upstream side toward a downstream side with respect to a direction a region of the belt-shaped body 11 continuous with the outer circumferential end 11f (described later) is pulled. The first region 21 is formed smooth. However, two projections 25A and 25B (collectively indicated by reference numeral 25 where appropriate) are formed in the second region 22 so as to catch on the outer cloth 4 and apply friction thereto. The projections 25A and 25B both extend along the length direction of the sleeve member 2, and are arranged along the circumference of the sleeve member 2. In this example, a gap between the projections 25A and 25B in the circumferential direction (an orientation angle from the center of the sleeve member 2) is set to approximately 30°. When viewed along the length direction of the sleeve member 2 as illustrated in FIG. 5D, tips of the projections 25A and 25B project at an angle away from a border 20 between the first region 21 and the second region 22, around the circumference of the sleeve member 2.

As illustrated in FIGS. 5A and 5B, indentations 27 and 28 are provided in specific locations (in this example, two locations on the left and right) of the upper portion 2A of the sleeve member 2 in the length direction thereof. These indentations 27 and 28 allow fluid within the air bladder 12 to flow in the circumferential direction X when using the cuff 1 to measure blood pressure.

As illustrated in FIG. 3A, the expanded portion 65 is provided around the first side 61 of the ring 6 in order to provide the ring 6 with the temporary fastening structure 60. Meanwhile, the sleeve member 2 is attached so as to be capable of pivoting around the second side 62 of the ring 6. Specifically, the upper portion 2A and the lower portion 2B of the sleeve member 2 are manufactured individually. Then, with the upper portion 2A of the sleeve member 2 facing the first side 61 of the ring 6 and the hole 29 surrounding the second side 62 of the ring 6, the upper portion 2A and the lower portion 2B are bonded to each other using an adhesive at the divided surface 2C. Note that the upper portion 2A and the lower portion 2B may be attached so as to be inseparable by providing a hook in one of the upper portion 2A and the lower portion 2B and a hole that engages with that hook in the other of these portions, with the hook entering into and engaging with the hole when the upper portion 2A and the lower portion 2B are combined.

As illustrated in FIG. 3C, a radius R of the cross-section of the sleeve member 2 to the outer circumferential surface 2S thereof (here, this refers to the outer circumferential surface of the upper portion 2A opposing the first side 61 of the ring 6) gradually becomes greater as the sleeve member 2 progresses circumferentially away from the border 20 between the first region 21 and the second region 22. As a result, when the sleeve member 2 rotates around the second side 62, the outer circumferential surface 2S of the sleeve member 2 functions as a first restricting element, making contact and engaging with the expanded portion 65 of the first side 61 (when the cuff 1 is in a completed state, the outer circumferential surface of the ring attachment member 7 or the outer cloth 4 of the belt-shaped body 11 that passes through the ring 6). In other words, the range in which the sleeve member 2 pivots around the second side 62 is restricted. As a result, the sleeve member 2 is fitted so as to be capable of pivoting around the second side 62. The temporary fastening structure 60 of the ring 6 is configured in this manner.

When performing temporary fastening, which will be described later, the temporary fastening structure 60 applies friction to the portion of the belt-shaped body 11 that passes through the ring 6 (more precisely, a gap 69 between the outer circumferential surface of the ring attachment member 7 and the outer circumferential surface 2S of the sleeve member 2) so as to suppress a case in which the region continuous with the outer circumferential end 11f of the belt-shaped body 11 is pulled back through the ring 6 by the elastic force of the measurement site.

As can be seen from FIG. 1 and, for example, FIG. 11 (mentioned later), the ring attachment member 7 includes a cylindrical portion 7a that surrounds the expanded portion 65 of the first side 61 of the ring 6 and a flat portion 7b for connecting the cylindrical portion 7a to the outer cloth 4. In this example, the cylindrical portion 7a is made from the same cloth material as the inner cloth 5 (the polyester cloth 51 on the front side and the polyurethane film 52 on the back side). The flat portion 7b is made from the same cloth material as the outer cloth 4 (the nylon cloth 41 on the front side, the tarpaulin layer 43 in the middle, and the polyurethane film 42 on the back side).

Figure 11:
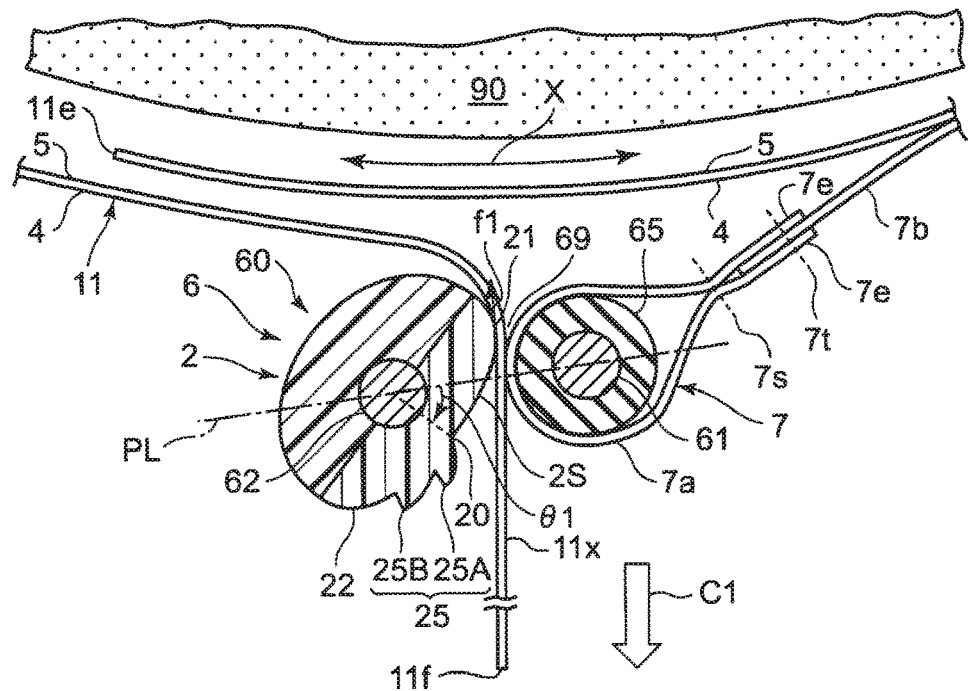
FIG. 11 is a cross-sectional view illustrating the vicinity of the ring in an enlarged state when the measurement subject pulls the belt-shaped body downward for the purpose of temporary fastening.

As illustrated in FIG. 11, in this example, the ring attachment member 7 is formed by folding back the cylindrical portion 7a so as to surround the expanded portion 65 of the first side 61 of the ring 6, placing the flat portion 7b between leading ends 7e and 7e of the cylindrical portion 7a, and then stitching along two lines 7s and 7t. The flat portion 7b is fixed by being welded to the region 4e on the inner circumferential end 11e side of the outer cloth 4 as shown in FIG. 1 (where a welded region 7m is indicated by hatching).

As a result of the ring 6 being attached using the ring attachment member 7, the ring 6 can pivot about the first side 61. Accordingly, the ring 6 can achieve a correct angle (orientation) relative to the belt-shaped body 11 that surrounds the measurement site when, for example, the cuff is worn, which will be described later.

Additionally, the outer cloth 4 of the belt-shaped body 11 is provided with a nipple 8 for supplying and evacuating air to and from the air bladder 12. The nipple 8 is welded to and attached at approximately the central portion of the outer cloth 4 (where a welded region 8m is indicated by hatching). An air tube 88 illustrated in FIG. 8 is connected to the nipple 8.

When the cuff 1 is shipped from the factory that manufactures the cuff 1, a region on the outer circumferential end 11f side of the belt-shaped body 11 where the hook-and-loop fastener 3 is provided (a region where the cuff as a whole is thicker than the belt-shaped body 11 by the thickness of the hook-and-loop fastener 3) is passed through the ring 6, giving the belt-shaped body 11 a substantially ring shape. In this case, when using the cuff, a user does not need to pass the outer circumferential end 11f of the belt-shaped body 11 through the ring 6 to the region where the hook-and-loop fastener 3 is provided, which eliminates that burden. Conversely, the hook-and-loop fastener 3 serves as a stopper and makes it difficult for the outer circumferential end 11f of the belt-shaped body 11 to pull out from the ring 6.

Figure 7:
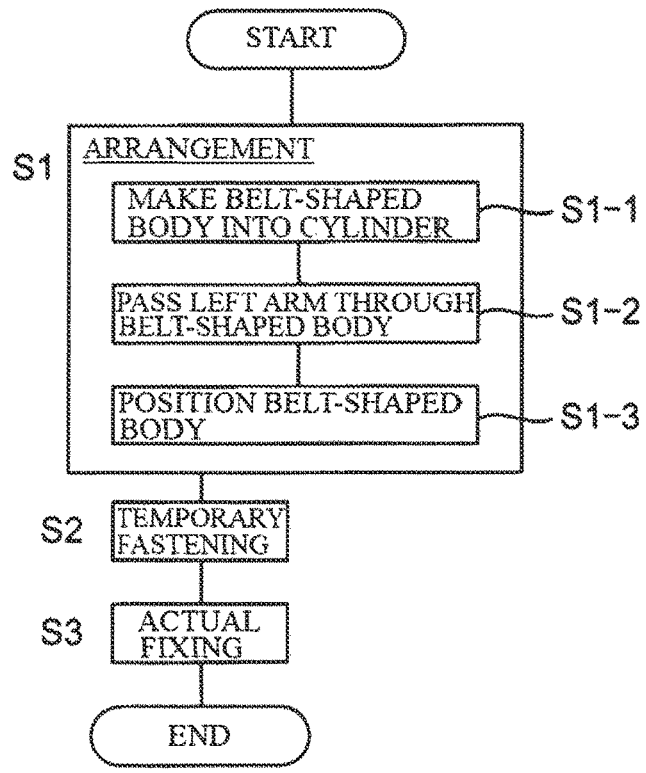
FIG. 7 is a diagram illustrating the flow of an attachment method for attaching the cuff to a left arm serving as a measurement site.

FIG. 7 illustrates the flow of an attachment method for attaching the cuff 1 to a left arm 90 serving as the measurement site. The attachment method is roughly executed by the measurement subject in the following order an arrangement step S1, a temporary fastening step S2, and an actual fixing step S3.

Figure 8:
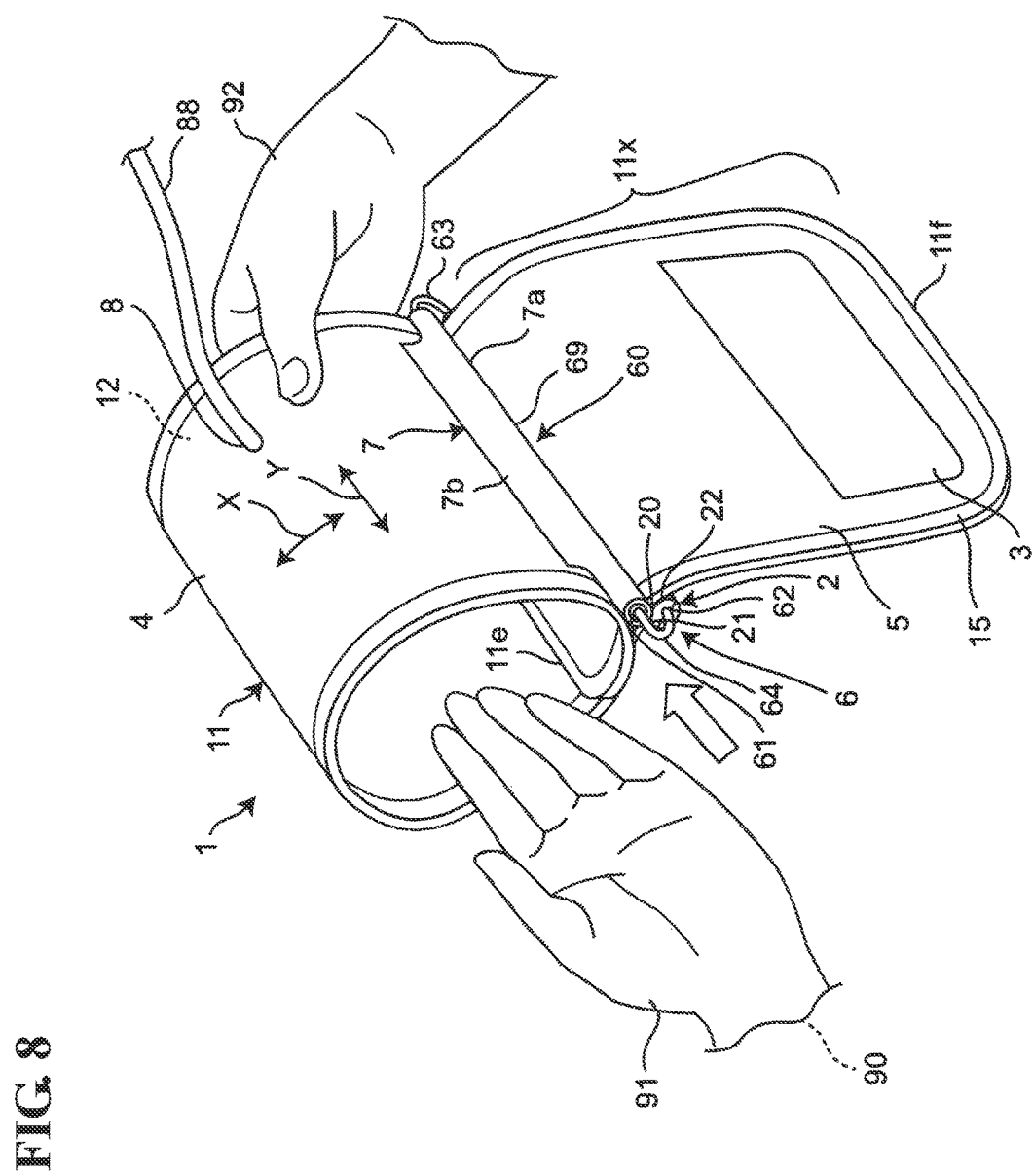
FIG. 8 is a diagram illustrating the execution of an arrangement step in the attachment method.

(1) In the arrangement step S1, as illustrated in FIG. 8, first, with the outer cloth 4 of the belt-shaped body 11 on the outer side, the measurement subject passes the region on the outer circumferential end 11f side of the belt-shaped body 11 where the hook-and-loop fastener 3 is provided through the ring 6, making the belt-shaped body 11 into a cylinder that is sufficiently wider than the left arm 90 (step S1-1 in FIG. 7).

Note that as illustrated in FIG. 3C, the outer circumferential surface 2S of the sleeve member 2 functions as the first restricting element and restricts the range in which the sleeve member 2 can pivot around the second side 62. The upper portion 2A of the sleeve member 2 is therefore always on the side that opposes the first side 61 of the ring 6. As such, the measurement subject need not be concerned about the angled position of the sleeve member 2 around the second side 62 when making the belt-shaped body 11 into a cylinder.

Next, as illustrated in FIG. 8, a left hand 91 to the left arm 90 is passed through the cylindrical belt-shaped body 11 from the side at which the cylindrical belt-shaped body 11 appears to the measurement subject to be in a counterclockwise spiral shape (counterclockwise from the inner circumferential end 11e to the outer circumferential end 11f) (step S1-2 in FIG. 7).

Next, the belt-shaped body 11 is adjusted so as to surround the upper arm area of the left arm 90 and, in this example, so that the ring 6 is positioned almost directly below the upper arm area of the left arm (step S1-3 in FIG. 7). Note that it is sufficient that the ring 6 be positioned below the upper arm area of the left arm, even if it is not exactly directly below the upper arm area of the left arm. In actuality, the position of the air tube 88 is set to the upper side. Alternatively, a mark may be provided on the cuff 1 (belt-shaped body 11) and aligned with the center of the arm, for example. Due to the structure of the cuff 1, the ring 6 will be located within a range spanning from below the arm to the right side of the arm when the cuff is attached in the correct position.

The left arm 90 is positioned in the cylindrical belt-shaped body 11 in this manner.

Figure 9:
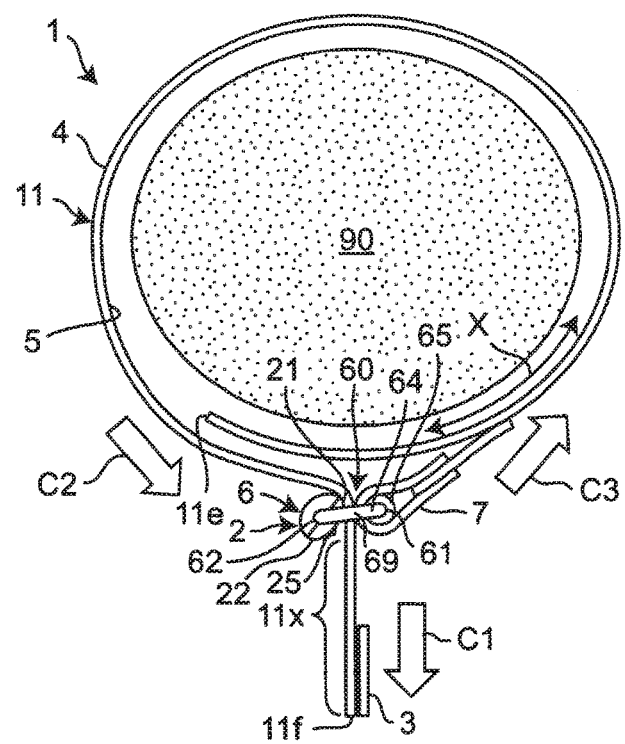
FIG. 9 is a diagram illustrating the execution of a temporary fastening step in the attachment method.

(2) In the temporary fastening step S2, as illustrated in FIG. 9, the measurement subject temporarily pulls the outer circumferential end 11f of the belt-shaped body 11 outward in a radial direction relative to the cylinder formed by the belt-shaped body 11 (a direction moving away from the left arm 90; in this example, in a direction C1 based on the position of the ring 6 relative to the left arm 90) with a right hand 92, substantially eliminating the gap between the inner cloth 5 of the belt-shaped body 11 and the left arm (this operation will be referred to as "temporary fastening" where appropriate). Note that arrows C2 and C3 in FIG. 9 respectively indicate the tensions received by the belt-shaped body 11 and the ring attachment member 7 under the arm strength of the right hand 92.

At this time, the ring 6 allows a region 11x continuous with the outer circumferential end 11f of the belt-shaped body 11 to be pulled through the ring 6 outward in the radial direction (the direction C1, in this example) with the arm strength of the right hand 92. Specifically, for example, it is assumed that at the start of the temporary fastening, the border 20 of the outer circumferential surface 2S of the sleeve member 2, between the first region 21 and the second region 22, is near a position opposing the first side 61 (this will be referred to as a "neutral position" where appropriate), as illustrated in FIG. 8. From the vicinity of this neutral position, as the region 11x continuous with the outer circumferential end 11f of the belt-shaped body 11 passes through the ring 6 and is pulled from the upstream side toward the downstream side, the sleeve member 2 fitted so as to be capable of pivoting around the second side 62 of the ring 6 rotates around the second side 62 and arrives at an angled position in which the first region 21 of the outer circumferential surface 2S of the sleeve member 2 opposes the first side 61 (this will be referred to as a "first angled position"), as illustrated in FIG. 11. At this time, the first region 21 of the sleeve member 2 functions as the first restricting element, making contact and engaging with the outer cloth 4 of the belt-shaped body 11 passing through the ring 6. The sleeve member 2 therefore stops at the first angled position. In this example, the first angled position is an angled position at which the border 20 between the first region 21 and the second region 22 is rotated, clockwise in FIG. 11, by an angle θ1 (θ1≈−45° in this example) relative to a plane PL containing the first side 61 and the second side 62 of the ring 6. The first region 21 makes contact with the outer cloth 4 of the belt-shaped body 11 as a result, and the belt-shaped body 11 slides along the outer cloth 4. At this time, friction f1 applied to the outer cloth 4 by the first region 21 is sufficiently lower than the arm strength pulling the belt-shaped body 11 and thus poses no problem. Accordingly, the measurement subject can more easily pull out the region 11x continuous with the outer circumferential end 11f of the belt-shaped body 11.

Meanwhile, in the cuff 1, the belt-shaped body 11 has a substantially uniform thickness. As such, during the operations of temporary fastening to the left arm 90 described above, the region 11x continuous with the outer circumferential end 11f of the belt-shaped body 11 traverses the gap 69 between the outer circumferential surface 2S of the sleeve member 2 and the outer circumferential surface of the ring attachment member 7 smoothly and is thus even more easily pulled out.

Also, with the cuff 1, the outer cloth 4 of the belt-shaped body 11 has the raised fibers 41a, and the raised fibers 41a are down-grain with respect to the direction in which the region 11x continuous with the outer circumferential end 11f is pulled through the ring 6. Accordingly, during the operations of temporary fastening to the left arm 90 described above, the region 11x continuous with the outer circumferential end 11f of the outer cloth 4 of the belt-shaped body 11 slides smoothly upon the first region 21 of the sleeve member 2 around the second side 62. Thus the region 11x continuous with the outer circumferential end 11f of the belt-shaped body 11 is even more easily pulled through the ring 6.

Additionally, at the portion of the outer circumferential surface of the ring attachment member 7 that forms the gap 69 with the outer circumferential surface 2S of the sleeve member 2 (that is, the cylindrical portion 7a), the raised fibers 41a are down-grain relative to the direction in which the region 11x continuous with the outer circumferential end 11f of the belt-shaped body 11 is pulled through the ring 6. As such, during the operations of temporary fastening to the left arm 90 described above, the region 11x continuous with the outer circumferential end 11f of the belt-shaped body 11 is easily pulled through the ring 6 even if the inner cloth 5 of the belt-shaped body 11 makes contact with the outer circumferential surface of the ring attachment member 7.

Figure 12:
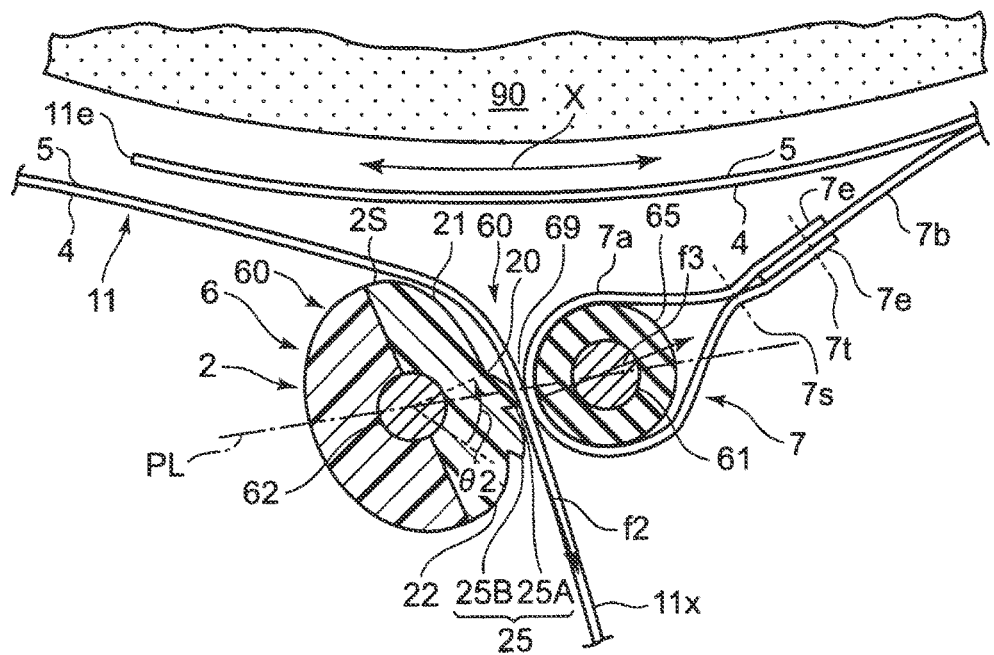
FIG. 12 is a cross-sectional view illustrating the vicinity of the ring in an enlarged state when the measurement subject relaxes the tensile force on the belt-shaped body after the temporary fastening operation.

After the above-described temporary fastening operations, it is assumed that the measurement subject relaxes the tensile force applied by his or her right hand. Upon doing so, the temporary fastening structure 60 of the ring 6 prevents the region 11x continuous with the outer circumferential end 11f of the belt-shaped body 11 pulled through using the arm strength of the right hand 92 from being pulled back through the ring 6 by the elastic force of the left arm 90. Specifically, when the region 11x continuous with the outer circumferential end 11f of the belt-shaped body 11 attempts to return through the ring 6 due to the elastic force of the left arm 90, the sleeve member 2 fitted so as to be capable of pivoting around the second side 62 of the ring 6 rotates around the second side 62 with the belt-shaped body 11 in the opposite direction as the pulling direction, and arrives at an angled position in which the second region 22 of the outer circumferential surface 2S of the sleeve member 2 opposes the first side 61 (this will be referred to as a "second angled position"), as illustrated in FIG. 12. At this time, the projections 25 of the second region 22 of the sleeve member 2 function as the first restricting element, making contact and engaging with the outer cloth 4 of the belt-shaped body 11 passing through the ring 6. The sleeve member 2 therefore stops at the second angled position. In this example, the second angled position is an angled position at which the border 20 between the first region 21 and the second region 22 is rotated, counterclockwise in FIG. 12, by an angle of approximately 15° relative to the plane PL containing the first side 61 and the second side 62 of the ring 6. To rephrase, the border 20 between the first region 21 and the second region 22 is at an angled position rotated, counterclockwise in FIG. 12, by an angle θ2 (θ2≈+60° in this example) from the first angled position (θ1≈−45°, indicated in FIG. 11). The belt-shaped body 11 slackens slightly with the rotation of the sleeve member 2 to the angle θ2. The amount of this slack is referred to as a "set slack amount Δ". Here, with the cuff 1, the projections 25 formed in the second region 22 (the projection 25A, in this example) make strong contact with the outer cloth 4 of the belt-shaped body 11 and apply a large amount of friction f2 thereon when the sleeve member 2 arrives at the second angled position (FIG. 12). Furthermore, when viewed along the length direction of the sleeve member 2 (in other words, as the cross-section indicated in FIG. 12), the tips of the projections 25 in the second region 22 project at an angle away from the border 20 between the first region 21 and the second region 22, around the circumference of the sleeve member 2. The tips of the projections 25 thus catch on the outer cloth 4 of the belt-shaped body 11 reliably and apply a large amount of friction f2 thereto. Accordingly, even if the measurement subject reduces the tensile force of the right hand 92, the belt-shaped body 11 slackening by an amount greater than the set slack amount Δ can be suppressed reliably.

The projections 25A and 25B of the sleeve member 2 are arranged within the second region 22 and extend along the length direction of the sleeve member 2. Accordingly, when the sleeve member 2 rotates around the second side 62 with the belt-shaped body 11 in the opposite direction as the direction of the pulling, one of the plurality of projections 25A and 25B formed so as to be arranged in the second region 22 of the sleeve member 2 catches on the outer cloth 4 of the belt-shaped body 11 and applies the friction f2. The belt-shaped body 11 slackening more than the set slack amount Δ can thus be suppressed reliably.

Additionally, in the example described above, the expanded portion 65 is provided around the first side 61 and the expanded portion 65 surrounds the ring attachment member 7; this makes it easy to set the dimension of the gap 69 between the outer circumferential surface 2S of the sleeve member 2 and the outer circumferential surface of the ring attachment member 7 (that is, the closest distance) in accordance with the thickness of the expanded portion 65 in the radial direction. The dimension of the gap 69 is set to be slightly greater than the thickness of the belt-shaped body 11.

Furthermore, a curvature factor of the outer circumferential surface of the ring attachment member 7 is lower than in a case where the expanded portion 65 is not provided. As a result, the distance between the outer circumferential surface 2S of the sleeve member 2 and the outer circumferential surface of the ring attachment member 7 in the direction in which the region 11x continuous with the outer circumferential end 11f of the belt-shaped body 11 passes changes little. This broadens the range in which the projections 25 of the second region 22 of the outer circumferential surface 2S of the sleeve member 2 can make contact with the outer cloth 4 of the belt-shaped body 11 in the direction in which the region 11x continuous with the outer circumferential end 11f of the belt-shaped body 11 traverses the gap 69 between the outer circumferential surface 2S of the sleeve member 2 and the outer circumferential surface of the ring attachment member 7, thus applying the friction f2 on the outer cloth 4 of the belt-shaped body 11 reliably. The belt-shaped body 11 slackening more than the set slack amount Δ can thus be suppressed reliably.

Meanwhile, the expanded portion 65 is made from an elastomer, which is an elastic material. Accordingly, when the sleeve member 2 rotates to the second angled position (FIG. 12) after the above-described temporary fastening operations, the sleeve member 2 receives a compressive force f3 from the projections 25 of the second region 22 via the belt-shaped body 11 and the ring attachment member 7 and elastically deforms, which reduces the curvature factor of the outer circumferential surface of the expanded portion 65. This further broadens the range in which the projections 25 of the second region 22 of the outer circumferential surface 2S of the sleeve member 2 can make contact with the outer cloth 4 of the belt-shaped body 11 in the direction in which the region 11x continuous with the outer circumferential end 11f of the belt-shaped body 11 traverses the gap 69 between the outer circumferential surface 2S of the sleeve member 2 and the outer circumferential surface of the ring attachment member 7, thus applying the friction f2 on the outer cloth 4 of the belt-shaped body 11 more reliably. The belt-shaped body 11 slackening more than the set slack amount Δ can thus be suppressed more reliably.

Additionally, with the cuff 1, the thickness of the belt-shaped body 11 is substantially uniform, and thus when the force with which the measurement subject pulls using the right hand 92 is relaxed after the above-described operations of temporary fastening to the left arm 90, the temporary fastening structure 60 of the ring 6 can reliably suppress a case in which the region 11x continuous with the outer circumferential end 11f of the belt-shaped body 11 is pulled back through the ring 6, regardless of the portion of the belt-shaped body 11 that is located in the ring 6, or in other words, regardless of the dimension in the circumferential direction X of the left arm 90.

Additionally, with the cuff 1, the raised fibers 41a of the outer cloth 4 are up-grain when the region 11x continuous with the outer circumferential end 11f of the belt-shaped body 11 attempts to return through the ring 6. The projections 25 of the second region 22 of the sleeve member 2 thus apply an even greater amount of friction to the outer cloth 4 of the belt-shaped body 11. Slackening in the belt-shaped body 11 can thus be more reliably suppressed.

Figure 10:
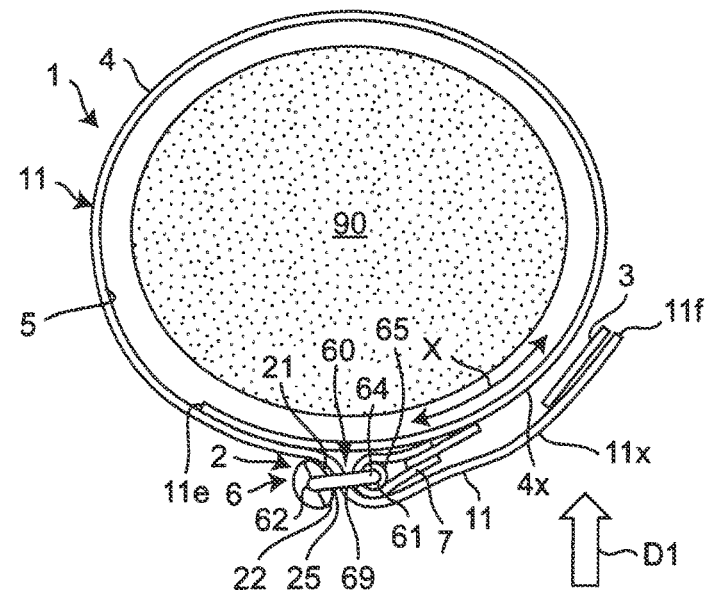
FIG. 10 is a diagram illustrating the execution of an actual fixing step in the attachment method.

(3) In the actual fixing step S3, as illustrated in FIG. 10, the measurement subject moves the right hand 92 in an upward direction DI at the torso side of the left arm 90 and, along the circumferential direction X of the left arm, brings the region 11x continuous with the outer circumferential end 11f of the belt-shaped body 11 into alignment with an orientation that is the same as that of the portion that has not passed through the ring 6 of the belt-shaped body 11. Accordingly, the hook-and-loop fastener 3 provided on the region 5f on the outer circumferential end 11f side of the inner cloth 5 is fixed to the portion 4x opposing the outer cloth 4 (this operation is referred to as "actual fixing" as appropriate).

Thus, the cuff 1 is attached in one direction along the circumferential direction X to the left arm 90 serving as the measurement site. That is to say, when viewed by the measurement subject along the length direction of the left arm 90, the cuff 1 is attached in a counterclockwise spiral shape.

Thus, the blood pressure measurement cuff 1 does not require an unnatural operation during attachment, unlike the case of the fold-back type of cuff 100 described above. In particular, during the above-described temporary fastening to the left arm, the measurement subject need only temporarily pull the outer circumferential end 11f of the belt-shaped body 11 outward in the radial direction (in the direction C1, in the above example) with the right hand 92. The operation for temporary fastening is not an operation in which the hand moves further laterally from the lateral side of the body, and there is no need for the measurement subject to continue to use his or her arm strength to maintain the tension of the belt-shaped body 11 until the actual fixing is complete. Accordingly, the measurement subject can easily attach the blood pressure measurement cuff 1 by himself or herself. For example, an obese person whose arm thickness makes it difficult to raise the arm outward from his or her body, an elderly person with little flexibility, or a sick person with little arm strength can perform the attachment relatively easily.

In the state of attachment after the actual fixing is complete, air is pumped into or evacuated from the air bladder 12 with a pump through the air tube 88 shown in FIG. 8, and the blood pressure is measured using the oscillometric method (in which the cuff itself acts as a pressure sensor and detects change in the pulse wave), for example. Note that a microphone may be built into the cuff 1 (the belt-shaped body 11) so as to measure the blood pressure based on a pulse sound observed using the microphone, according to the Korotkoff method.

Also, in the state of being attached after the actual fixing is complete, the blood pressure measurement cuff 1 is wrapped around the left arm 90 in one direction along the circumferential direction X. In other words, in the entire region along the circumferential direction X of the left arm 90, the inner cloth 5 is hidden, and only the outer cloth 4 can be seen on the front side. As described above, the outer cloth 4 is set such that it has less elasticity than the inner cloth 5 (or is not elastic). In this case, when air is pumped into the air bladder 12 with a pump for blood pressure measurement, with the blood pressure measurement cuff 1, the cloth seen on the front side (the outer cloth 4) does not needlessly inflate outward (to the side opposite to the left arm 90). Accordingly, it is possible to suppress the amount of air supplied to the air bladder 12, thereby increasing the efficiency of pressurization.

Also, with the blood pressure measurement cuff 1, the cloth seen on the front side (the outer cloth 4) never needlessly inflates outward, and therefore the measurement subject is never caused to feel uneasy.

Furthermore, with the blood pressure measurement cuff 1, since the cloth seen on the front side (outer cloth 4) never needlessly inflates outward, an arrangement is possible in which the air bladder 12 is extended over most of the region in the circumferential direction X (length direction) in the belt-shaped body 11. With this kind of arrangement, there is no longer a restriction on the extension range of the air bladder in the circumferential direction in the case of a fold-back type of cuff 100 (described above), whereby the range of dimensions in the circumferential direction of the measurement site set as specifications of the cuff 1 (refers to a range ranging from a minimum circumference to a maximum circumference) can be widened.

For example, assuming the range of dimensions in the circumferential direction of the measurement site is from 22 cm to 32 cm in the specifications of the fold-back type of cuff 100, the range of dimensions in the circumferential direction of the measurement site can be widened to 17 cm to 36 cm, for example, in the specifications of the cuff 1. As long as the dimension of the measurement subject's left arm 90 in the circumferential direction is within this range, the air bladder 12 of the belt-shaped body 11 can surround the entire circumference of the left arm 90.

Also, it is known that the compression force compressing the artery of the left arm 90 relies on the dimension in the circumferential direction X of the air bladder 12 and the dimension in the width direction Y that intersects the circumferential direction X. The larger the dimension in the circumferential direction and the dimension in the width direction of the air bladder 12 are, the larger the compression force is. Here, as illustrated in FIGS. 1 and 2, according to the arrangement in which the air bladder 12 is extended over most of the region in the circumferential direction X, the dimension in the width direction of the air bladder 12 can be reduced instead in order to obtain the required compression force. If the dimension in the width direction of the air bladder 12 is thus reduced, and the dimension in the width direction of the belt-shaped body 11 is accordingly reduced, the measurement subject can more easily attach the blood pressure measurement cuff 1. For example, assuming the dimension in the width direction of the cuff is 125 mm in the specifications of the fold-back type of cuff 100, in the specifications of the cuff 1, the dimension in the width direction of the cuff (belt-shaped body) can be reduced to 115 mm, for example. Also, if the dimensions in the width direction of the air bladder 12 and the belt-shaped body 11 are reduced, the cost of materials can be reduced. Accordingly, the blood pressure measurement cuff 1 can be produced at a low cost.

Meanwhile, as illustrated in FIGS. 5A and 5B, in the cuff 1, the indentations 27 and 28, which allow the fluid within the air bladder 12 to flow in the circumferential direction X, are provided in the outer circumferential surface 2S of the sleeve member 2 that surrounds the second side 62, on the side thereof that opposes the first side 61, and in specific locations (two locations, in this example) with respect to the length direction. Accordingly, in the case where an arrangement in which the air bladder 12 is extended over most of the region in the circumferential direction X (length direction) in the belt-shaped body 11 as described above is employed, the indentations 27 and 28 allow the fluid within the air bladder 12 to flow in the circumferential direction X. Thus the fluid can be supplied and evacuated smoothly across the entirety of the air bladder 12 in the circumferential direction X. Blood pressure measurements can be taken smoothly using the blood pressure measurement cuff 1 as a result.

Meanwhile, in the case where the expanded portion 65 is provided around the first side 61 as in the above example, it is desirable that a ring-shaped indentation following the outer circumference of the expanded portion 65 be provided in a specific location with respect to the length direction of the expanded portion 65 so as to allow the flow of the fluid within the air bladder 12 in the circumferential direction X (the first side 61 may be partially exposed by this indentation). In this case, it is desirable that a cutout be provided in a region of the ring attachment member 7 corresponding to the indentation in the expanded portion 65. In other words, as a result, the fluid can be supplied and evacuated smoothly across the entirety of the air bladder 12 in the circumferential direction X. Blood pressure measurements can be taken smoothly using the blood pressure measurement cuff 1 as a result.

When the measurement subject removes the cuff 1 from the left arm 90, first, the measurement subject separates the hook-and-loop fastener 3 provided on the region 5f on the outer circumferential end 11f side of the inner cloth 5 from the opposing portion on the outer cloth 4 with the right hand 92 (actual fixing removal). Next, for example, the measurement subject inserts a finger of his or her right hand 92 between the belt-shaped body 11 and the left arm 90 and applies a pressure greater than the friction f2 applied by the second region 22 of the sleeve member 2, so that the cylinder diameter of the belt-shaped body 11 widens. Upon doing so, the region 11x continuous with the outer circumferential end 11f of the belt-shaped body 11 is pulled back through the ring 6 without receiving the friction f2 from the second region 22. Accordingly, the belt-shaped body 11 becomes a cylinder that is sufficiently wider than the left arm 90 (temporary fastening removal). Thereafter, the cuff 1 is removed from the left arm 90.

Note that in order to carry out the temporary fastening removal, the measurement subject may grip the sleeve member 2 around the second side 62 of the ring 6 with his or her right hand 92 and rotate the sleeve member 2 around the second side 62 to the first angled position (FIG. 11). Specifically, the first region 21 of the outer circumferential surface 2S of the sleeve member 2 is placed opposite the first side 61 and in contact with the outer cloth 4 of the belt-shaped body 11. In this state, the measurement subject uses his or her right hand 92 to pull the sleeve member 2 in a direction away from the left arm 90 (the direction C1, in this example) along with the second side 62 of the ring 6. Upon doing so, the region 11x continuous with the outer circumferential end 11f of the belt-shaped body 11 slides upon the first region 21 of the outer circumferential surface 2S of the sleeve member 2 and is easily pulled back through the ring 6. Accordingly, the belt-shaped body 11 becomes a cylinder that is sufficiently wider than the left arm 90 (temporary fastening removal).

Note that if the right arm is to be used as the measurement site instead of the left arm 90, it is sufficient that a cuff with a left-right inverted structure is created and the above description of the method for attachment to the left arm and the method for removal are read replacing "left" with "right". Also, it is sufficient that the measurement site be a site that can be wrapped by the cuff 1, and may be a wrist or a leg, for example.

Variations

When, as a result of the above-described temporary fastening operations, the sleeve member 2 rotates around the second side 62 as the region 11x continuous with the outer circumferential end 11f of the belt-shaped body 11 is pulled out as illustrated in FIG. 11, it is possible that the belt-shaped body 11 will become caught in the gap 69 between the outer circumferential surface 2S of the sleeve member 2 and the outer circumferential surface of the ring attachment member 7 and receive friction that cannot be ignored.

FIG. 13A illustrates the ring 6 having a temporary fastening structure 60' according to a variation for handling this issue, and is a view seen from approximately the same side as in FIG. 2. FIG. 13B illustrates the ring 6 shown in FIG. 13A from the right side. FIG. 13C illustrates a cross-section taken along line C-C in FIG. 13A. The ring 6 having the temporary fastening structure 60' differs only in that a sleeve member 2' having pins 23 and 24 is provided as a second restricting element instead of the sleeve member 2 described above.

Figure 14A:
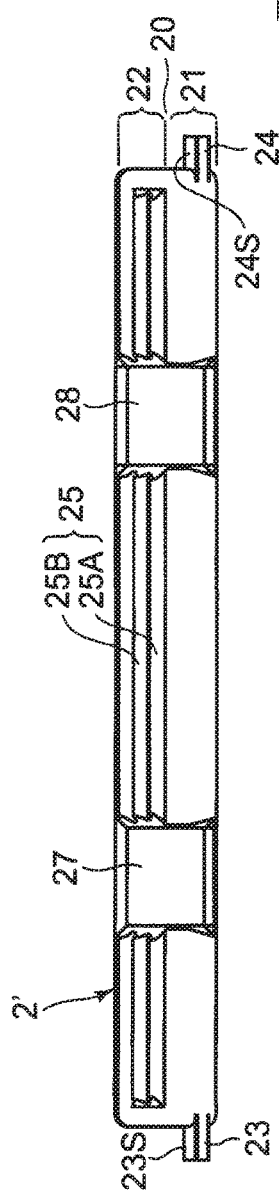
FIG. 14A is a diagram illustrating the sleeve member shown in FIG. 14B from above.
Figure 14B:
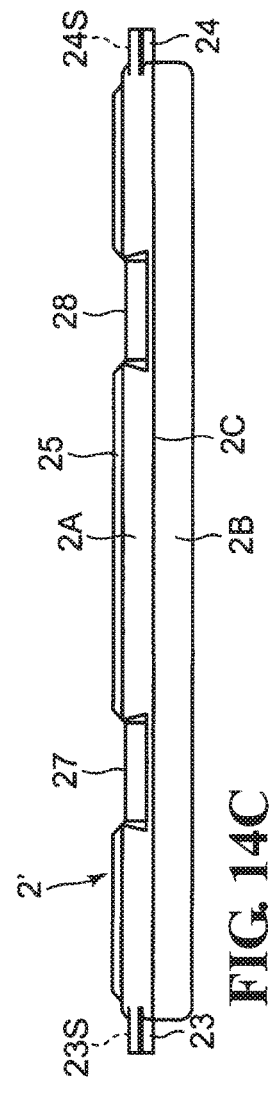
FIG. 14B is a diagram illustrating a sleeve member shown in FIG. 13A alone.
Figure 14C:
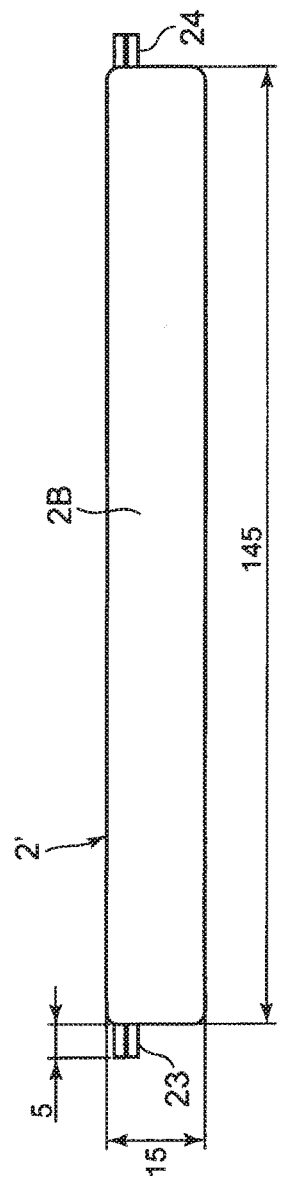
FIG. 14C is a diagram illustrating the sleeve member shown in FIG. 14B from below.
Figure 14D:
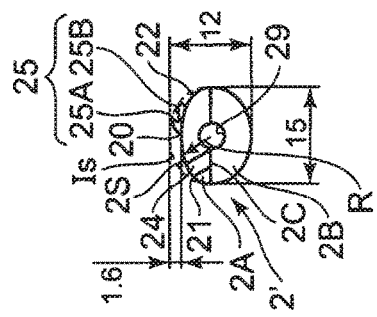
FIG. 14D is a diagram illustrating the sleeve member shown in FIG. 14B from the right side.

FIGS. 14A to 14D illustrate the sleeve member 2' alone, and correspond to FIGS. 5A to 5D. In FIGS. 14A to 14C, the pins 23 and 24 are formed integrally with the sleeve member 2', and project from end surfaces of the sleeve member 2' in the length direction thereof with horizontal symmetry. In this example, the dimensions at which the pins 23 and 24 project are both set to 5 mm. As illustrated in FIG. 14D, the pin 24 (and 23) is disposed on a predetermined location corresponding to the first region 21, around the center of the sleeve member 2'. Specifically, in FIG. 13B (where the sleeve member 2' is in the neutral position, where the border 20 between the first region 21 and the second region 22 of the outer circumferential surface 2S opposes the first side 61), the pins 23 and 24 are disposed so that when the sleeve member 2' is rotated clockwise by approximately 30°, side surfaces 23S and 24S of the pins 23 and 24 make contact and engage with the connecting portions 63 and 64 of the ring 6.

Note that constituent elements in FIGS. 13 and 14 (and in FIGS. 15 and 16, mentioned later) identical to the constituent elements already described are given the same reference numerals, and redundant descriptions are omitted.

Figure 15A:
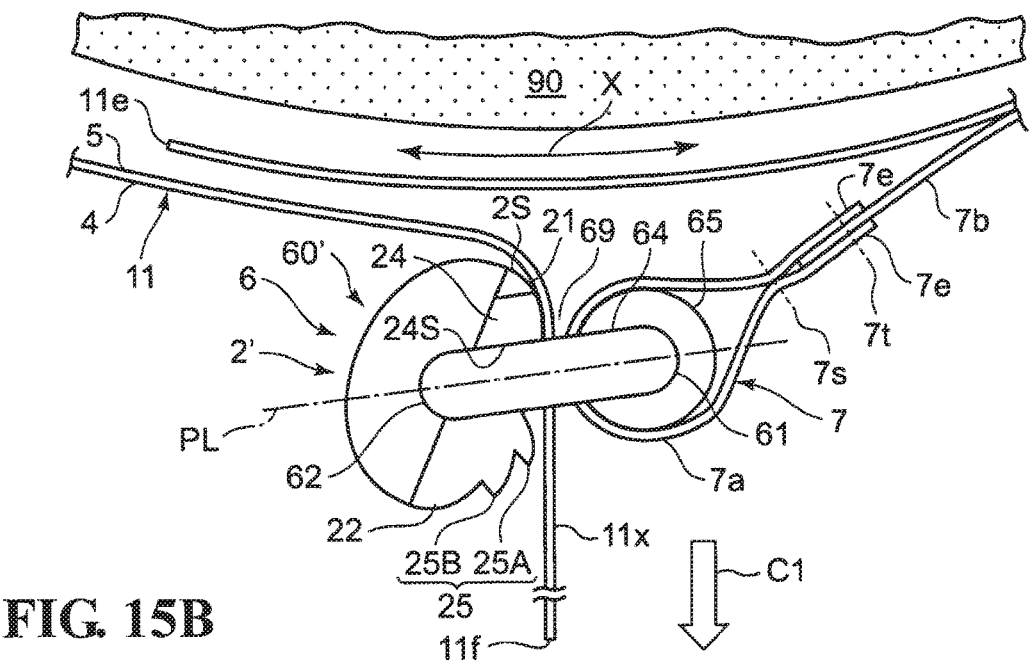
FIG. 15A is a diagram illustrating a case where the cuff includes the ring illustrated in FIG. 13, and illustrates the vicinity of the ring from the side when the measurement subject pulls the belt-shaped body downward for the purpose of temporary fastening.
Figure 15B:
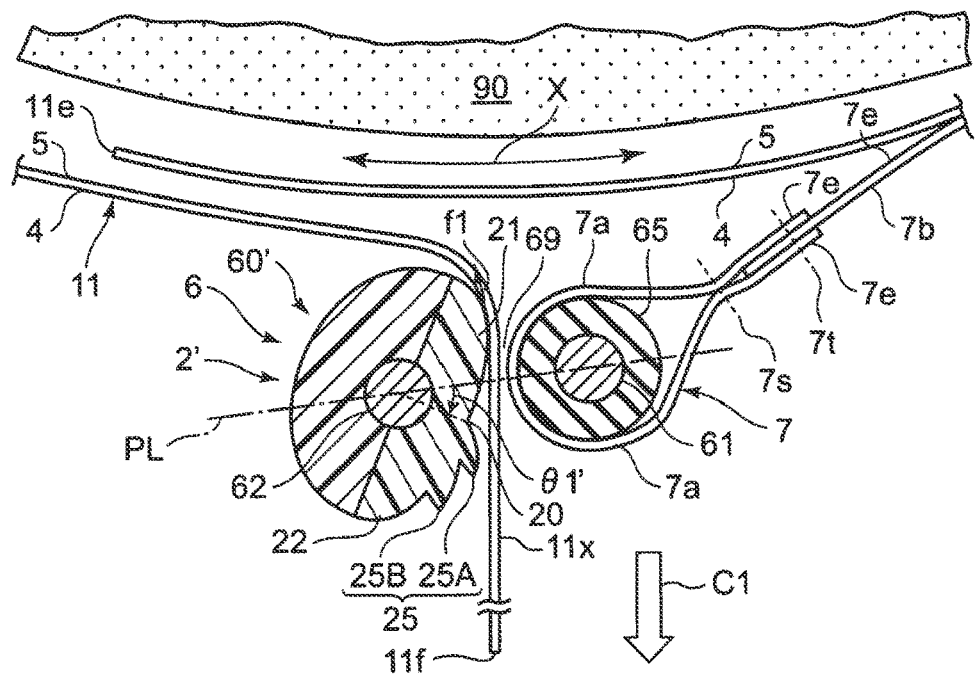
FIG. 15B is a cross-sectional view corresponding to FIG. 15A.

FIG. 15A illustrates, in the case where the above-described cuff includes the ring 6 having the temporary fastening structure 60' illustrated in FIG. 13, the vicinity of the ring 6 from the side, when the measurement subject pulls the outer circumferential end 11f of the belt-shaped body 11 outward in the radial direction relative to the cylinder formed by the belt-shaped body 11 (the direction C1, in this example) for the purpose of temporary fastening. FIG. 15B illustrates a cross-section corresponding to FIG. 15A.

As illustrated in FIG. 15A, the sleeve member 2 engaged so as to be capable of pivoting around the second side 62 of the ring 6 rotates around the second side 62 as the region 11x continuous with the outer circumferential end 11f of the belt-shaped body 11 is pulled through the ring 6 from the upstream side toward the downstream side. Upon doing so, as described above, the side surfaces 23S and 24S of the pins 23 and 24 function as the second restriction element, making contact and engaging with the connecting portions 63 and 64 of the ring 6. Accordingly, as illustrated in FIG. 15B, the first angled position at which the sleeve member 2' stops is restricted to an angled position closer to the aforementioned neutral position than the angled position determined by the outer circumferential surface 2S of the sleeve member 2' serving as the first restricting element. In this example, the first angled position is an angled position at which the border 20 between the first region 21 and the second region 22 is rotated, clockwise in FIG. 15B, by an angle θ1' (θ1'≈−30° in this example) relative to the plane PL containing the first side 61 and the second side 62 of the ring 6. Accordingly, the gap 69 can be secured between the outer circumferential surface 2S of the sleeve member 2' and the outer circumferential surface of the ring attachment member 7, and a situation in which the belt-shaped body 11 is caught in the gap 69 between the outer circumferential surface 2S of the sleeve member 2 and the outer circumferential surface of the ring attachment member 7 can be avoided. As a result, the measurement subject can easily pull out the region 11x continuous with the outer circumferential end 11f of the belt-shaped body 11 through the ring 6.

Figure 16A:
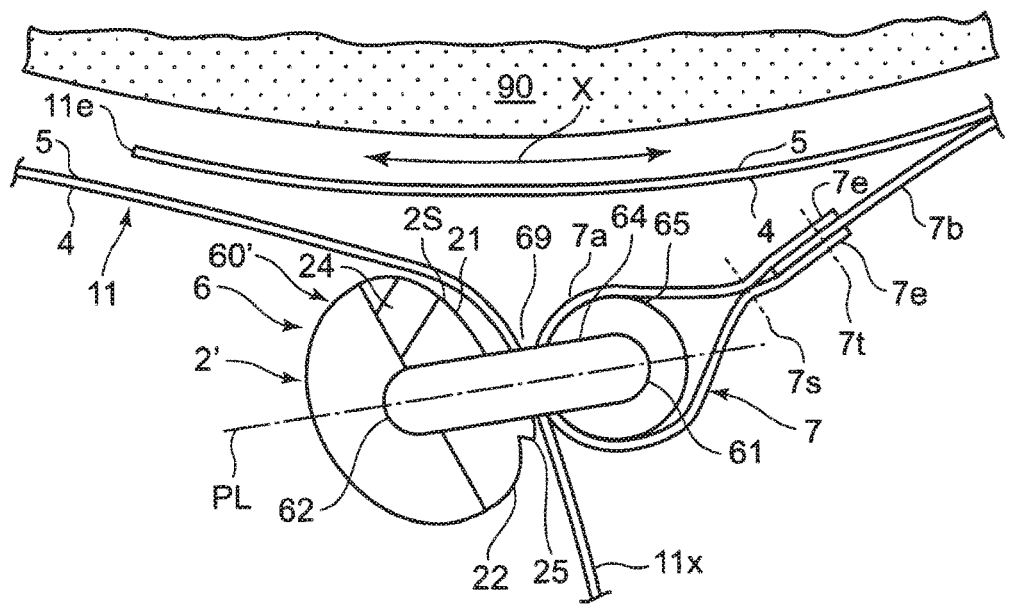
FIG. 16A is a diagram illustrating a case where the cuff includes the ring illustrated in FIG. 13, and illustrates the vicinity of the ring from the side when the measurement subject relaxes the tensile force on the belt-shaped body after the temporary fastening operation.
Figure 16B:
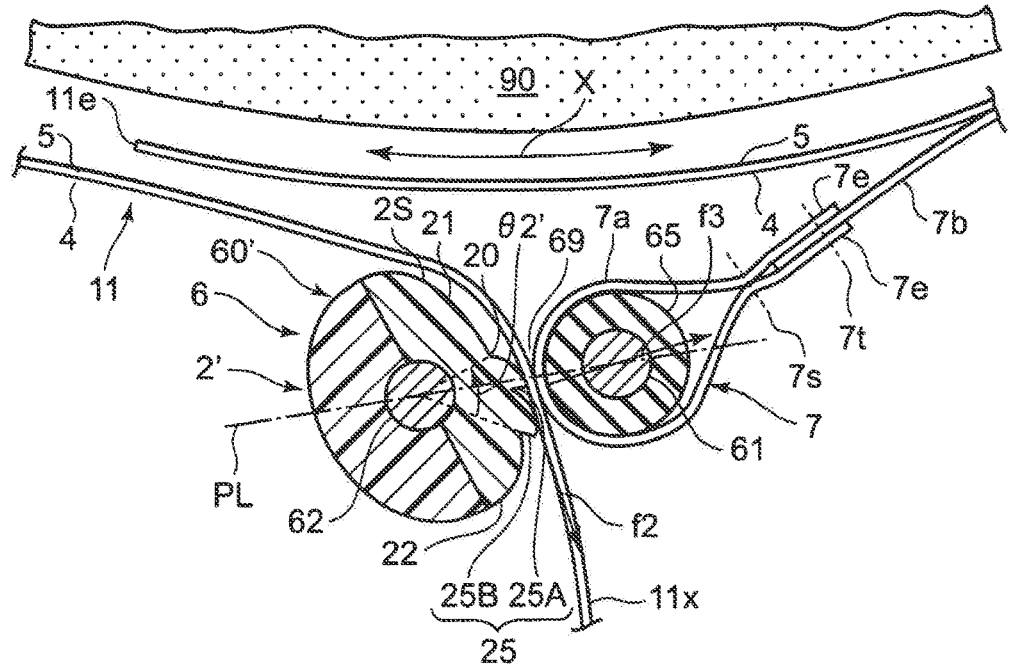
FIG. 16B is a cross-sectional view corresponding to FIG. 16A.

FIG. 16A illustrates a case where the cuff includes the ring 6 having the temporary fastening structure 60' shown in FIG. 13, and illustrates the vicinity of the ring 6 from the side when the measurement subject relaxes the tensile force on the belt-shaped body 11 after the temporary fastening operation. FIG. 16B illustrates a cross-section corresponding to FIG. 16A.

As illustrated in FIG. 16B, when the measurement subject relaxes the tensile force on the belt-shaped body 11, the sleeve member 2 fitted so as to be capable of pivoting around the second side 62 of the ring 6 rotates around the second side 62 with the belt-shaped body 11, in the opposite direction as during the pulling, and the second region 22 of the outer circumferential surface 2S of the sleeve member 2 arrives at the second angled position opposing the first side 61 and stops. In this example, the second angled position is, as in the example described earlier (FIG. 12), an angled position at which the border 20 between the first region 21 and the second region 22 is rotated, counterclockwise in FIG. 16B, by an angle of approximately 15° relative to the plane PL containing the first side 61 and the second side 62 of the ring 6. To rephrase, at the second angled position, the border 20 between the first region 21 and the second region 22 is at an angled position rotated, counterclockwise in FIG. 12, by an angle θ2' (θ2'≈+45° in this example) from the first angled position (θ1'≈−30°, indicated in FIG. 15B). The belt-shaped body 11 slackens slightly with the rotation of the sleeve member 2 to the angle θ2'. An amount of slack corresponding to this angle θ2' (≈+45°) (that is, a set slack amount Δ') is lower than the set slack amount Δ corresponding to the angle θ2 (≈+60°) of the earlier example.

In this manner, in the case where the ring 6 having the temporary fastening structure 60' according to this variation is provided, the first angled position is an angled position closer to the neutral position (θ1'≈−30°), and thus the set slack amount can be reduced. Slackening in the belt-shaped body 11 between the above-described temporary fastening operations and the actual fixing can therefore be further suppressed.

Note that the pins 23 and 24 in the end surfaces of the sleeve member 2' may be disposed closer to the border 20 between the first region 21 and the second region 22. For example, the pins 23 and 24 may be disposed so that the side surfaces 23S and 24S thereof make contact and engage with the connecting portions 63 and 64 of the ring 6 when the sleeve member 2' is rotated clockwise by approximately 15° in FIG. 13B. In this case, when the measurement subject relaxes the tensile force on the belt-shaped body 11 after the above-described temporary fastening operations, the angle θ2' that provides the set slack amount Δ' becomes approximately +30°, which is even lower than in the above example (θ2'≈+45°). Slackening in the belt-shaped body 11 between the above-described temporary fastening operations and the actual fixing can therefore be further suppressed.

Like the sleeve member 2, the sleeve member 2' has a generally elliptical cross-section in this variation. However, one or more embodiments of the present invention are not limited thereto. The first region 21 of the upper portion 2A in particular may have a constant cross-sectional radius R (the same as the radius at the border 20 between the first region 21 and the second region 22). As a result, the possibility of the belt-shaped body 11 being caught in the gap 69 between the outer circumferential surface 2S of the sleeve member 2 and the outer circumferential surface of the ring attachment member 7 as the region ix continuous with the outer circumferential end 11f of the belt-shaped body 11 is pulled out can be eliminated.

Additionally, in this variation, the pins 23 and 24 are added as the second restriction element, in addition to the outer circumferential surface 2S of the sleeve member 2' serving as the first restricting element, in order to restrict the pivoting range of the sleeve member 2'. However, one or more embodiments of the present invention are not limited thereto. For example, pins may be provided in locations of the end surfaces of the sleeve member that corresponding to the first region 21 and the second region 22, respectively, and the range in which the sleeve member pivots around the second side 62 may be restricted using those pins only. In this case, it is desirable that the pin corresponding to the second region 22 be disposed in a location, in the end surface of the sleeve member, that is further from the border 20 between the first region 21 and the second region 22 than the location corresponding to the projection 25, to avoid interfering with the function of the projection 25.

Manufacturing Method

FIGS. 17A1 and 17A2 to 17D illustrate a method for manufacturing the cuff 1 (these drawings correspond to cross-sections taken along the width direction Y in FIG. 1).

First, as illustrated in FIG. 17A1, the above-described nylon cloth 41, a tarpaulin fabric 43' serving as the material of the tarpaulin layer 43, and the polyurethane film 42 are prepared as materials of the outer cloth 4. As illustrated in FIG. 17B1, the tarpaulin fabric 43' is affixed to the back side (knitted fabric 41b side) of the nylon cloth 41 using melted polyvinyl chloride (PVC) as an adhesive, forming the tarpaulin layer 43 containing PVC in the gaps between the threads of the tarpaulin fabric 43'. Furthermore, the polyurethane film 42 is bonded to the back side of the tarpaulin layer 43 using an adhesive (not shown). The outer cloth 4 is formed as a result. Meanwhile, as illustrated in FIGS. 17A2 and B2, the above-described polyester cloth 51 and polyurethane film 52 are prepared as materials of the inner cloth 5, and the polyurethane film 52 is bonded to the back side of the polyester cloth 51 using an adhesive (not shown). The inner cloth 5 is formed as a result.

Note that the nipple 8 and the flat portion 7b of the ring attachment member 7 illustrated in FIG. 1 are attached to the outer cloth 4 at this stage.

Next, as illustrated in FIG. 17C, the inner cloth 5 and the outer cloth 4 are overlaid opposite each other with the polyurethane films 42 and 52 interposed therebetween.

Next, as illustrated in FIG. 17D, the inner cloth 5 and the outer cloth 4 are heated and welded at the regions 11m and 11n indicated by hatching in FIG. 1.

Accordingly, the belt-shaped body 11 containing the air bladder 12 serving as the fluid bladder is formed between the inner cloth 5 and the outer cloth 4. The thickness of the belt-shaped body 11 is made substantially uniform.

Next, the ring 6 having the expanded portion 65 on the first side 61 (in the state illustrated in FIG. 4B) is prepared. Then, as illustrated in FIG. 11, the cylindrical portion 7a of the ring attachment member 7 is folded back so as to surround the expanded portion 65 of the first side 61 of the ring 6, the flat portion 7b is placed between the leading ends 7e and 7e of the cylindrical portion 7a, and then stitches are made along two lines 7s and 7t. The ring 6 is attached to the belt-shaped body 11 via the ring attachment member 7 as a result.

Then, as illustrated in FIG. 8, the belt-shaped body 11 is passed through the ring 6 (and more precisely, between the cylindrical portion 7a of the ring attachment member 7 and the second side 62) from the outer circumferential end 11f thereof to the region where the hook-and-loop fastener 3 is provided (the belt-shaped body 11 becomes substantially ring-shaped as a result). In this state, the upper portion 2A and the lower portion 2B (see FIGS. 5D and 14D, for example) of the sleeve member 2 or 2', which have been made in advance, are bonded to each other, around the second side 62 of the ring 6 with the upper portion 2A opposing the first side 61, using an adhesive, for example. This attaches the sleeve member 2 or 2' so as to be capable of pivoting around the second side 62 of the ring 6.

This completes the manufacture of the cuff 1 described above. When shipping from the factory, the cuff is shipped with the belt-shaped body 11 remaining folded over in a substantially ring shape.

Note that FIGS. 18A to 18D illustrate a method for manufacturing a typical belt-shaped body 110.

Figure 18A:
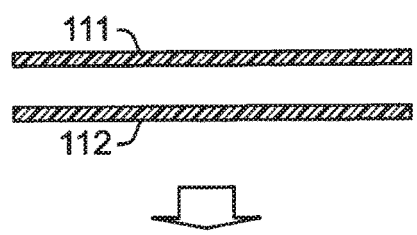
FIGS. 18A to 18D are process diagrams illustrating a method of manufacturing a typical belt-shaped body.

First, as illustrated in FIG. 18A, PVC films 111 and 112 are prepared as materials of the air bladder 102.

Figure 18B:
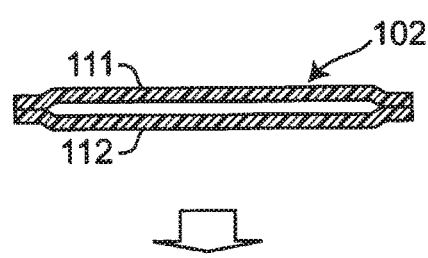

Next, as illustrated in FIG. 18B, the PVC films 111 and 112 are overlaid opposite each other. The PVC films 111 and 112 are then welded together at peripheral edge regions of the PVC films. The air bladder 102 is formed as a result.

Figure 18C:
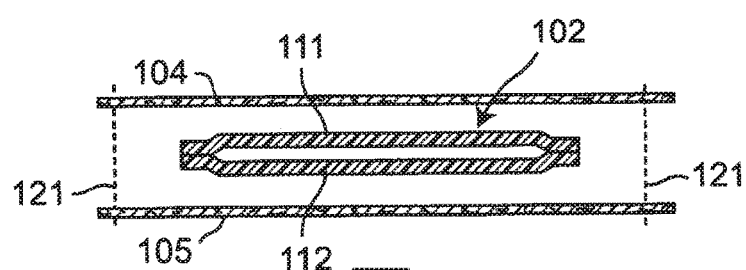

Next, as illustrated in FIG. 18C, an inner cloth 105 and an outer cloth 104 having dimensions in the circumferential direction and width direction that are greater than the dimensions of the air bladder 102 are prepared, and the inner cloth 105 and outer cloth 104 are arranged opposite each other with the air bladder 102 interposed therebetween.

Figure 18D:
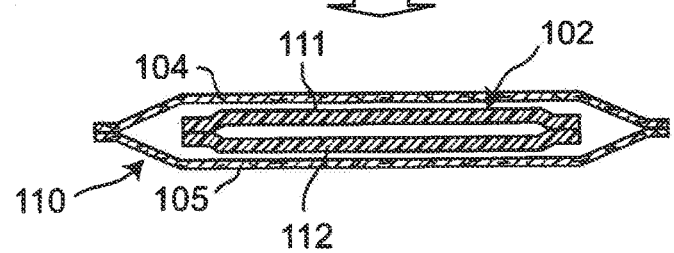
Figure 19A:
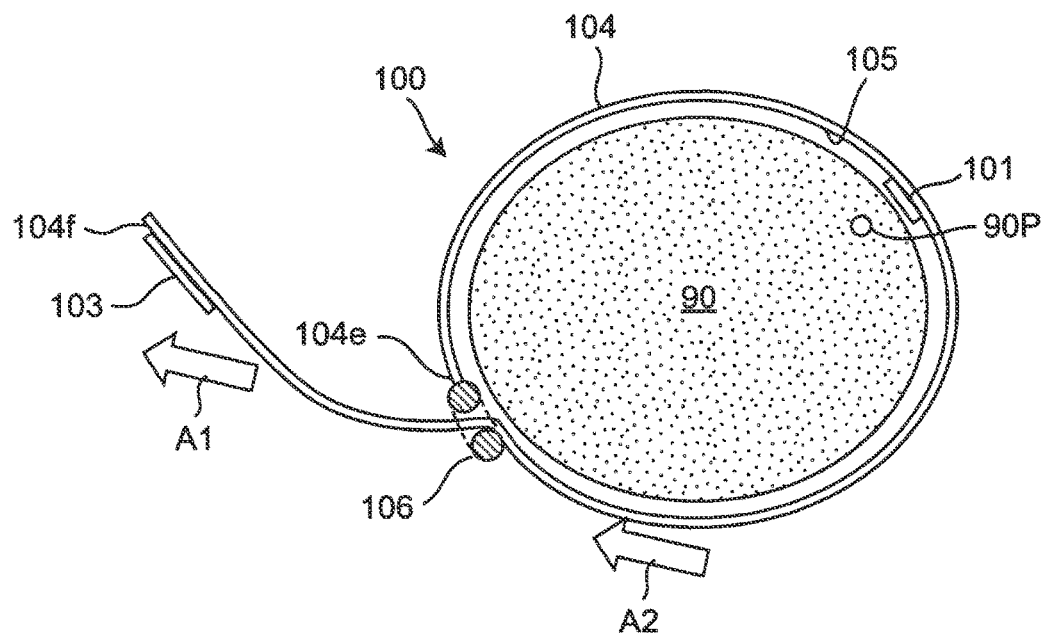
FIGS. 19A and 19B are diagrams illustrating a method of attaching a conventional cuff.
Figure 19B:
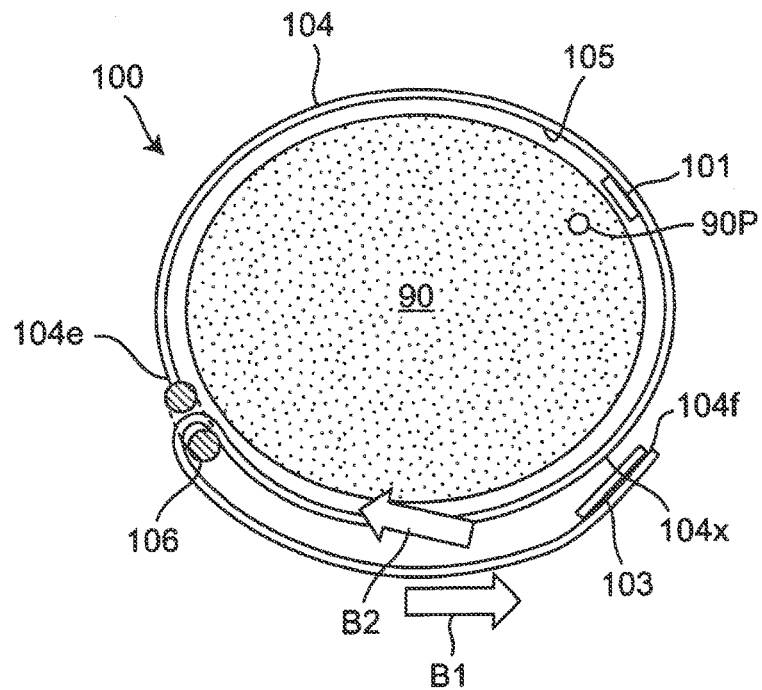

Then, as illustrated in FIG. 18D, the inner cloth 105 and outer cloth 104 are made into a bag shape by sewing peripheral edges 121 thereof together. Note that an edge portion cover 15 such as that illustrated in FIG. 8 may be provided along the peripheral edges 121.

With the typical belt-shaped body 110 formed in this way, there is a difference in the overall thickness of the cuff between the region in which the air bladder 102 exists and the regions in which it does not exist, and level differences in the external shape appear at the borders between the region in which the air bladder 102 exists and the regions in which it does not exist. In this case, in the ring 6 having the above-described temporary fastening structure 60 or 60', it is desirable that the dimension of the gap 69 between the outer circumferential surface 2S of the sleeve member 2 and the outer circumferential surface of the ring attachment member 7 (that is, the closest distance) be set to be slightly greater than the maximum thickness of the belt-shaped body 110 (the thickness of the regions where the air bladder 102 is present).

Although there are two projections 25 (25A and 25B) in the second region 22 of the sleeve member 2 in the above-described examples, one or more embodiments of the invention are not limited thereto. In the second region 22 of the sleeve member 2, three or more projections 25 may be arranged along the circumference of the sleeve member. In this case, after the above-described temporary fastening operations, when the sleeve member 2 rotates around the second side 62 with the belt-shaped body 11 in the opposite direction as the direction of the pulling, one of the three or more projections 25 catches on the outer cloth 4 of the belt-shaped body 11 and applies friction. The belt-shaped body 11 slackening more than the set slack amount can thus be suppressed reliably. Note that there may be one projection 25 as well.

The embodiments described above are examples, and can be carried out with various modifications without departing from the scope of the invention. The multiple embodiments described above can function on their own, but embodiments may be combined with each other. Additionally, various features of different embodiments can function on their own, but features of different embodiments can also be combined with each other.

REFERENCE SIGNS LIST 1 blood pressure measurement cuff
2, 2' sleeve member
21 first region
22 second region
23, 24 pin
25, 25A, 25B projection
27, 28 indentation
3 hook-and-loop fastener
4 outer cloth
5 inner cloth
6 ring
7 ring attachment member
11 belt-shaped body
60, 60' temporary fastening structure
61 first side
62 second side
63, 64 connecting portion
65 expanded portion

The invention claimed is:

1. A blood pressure measurement cuff to be wrapped in one direction along a circumferential direction around a measurement site, the blood pressure measurement cuff comprising:
   a belt-shaped body obtained by enveloping a fluid bladder with an inner cloth to be in contact with the measurement site and an outer cloth opposing the inner cloth;

a ring attached via a ring attachment member to a region on an inner circumferential end side of the outer cloth; and a hook-and-loop fastener provided in a region on an outer circumferential end side of the inner cloth and fixed detachably to the outer cloth, wherein the ring includes a first side that extends in a direction intersecting the circumferential direction, a second side that extends along the first side, and a pair of connecting portions that connect ends of the first and second sides, and at least a portion of the first side is attached to a region on the inner circumferential end side of the outer cloth so as to be surrounded by the ring attachment member;

the ring has a temporary fastening structure that allows a region continuous with an outer circumferential end of the belt-shaped body to be pulled through the ring with arm strength away from the measurement site during attachment and suppresses a case in which a region continuous with the outer circumferential end of the belt-shaped body pulled by the arm strength is pulled back through the ring by elastic force of the measurement site;

the temporary fastening structure has a sleeve member fitted around the second side so as to be capable of pivoting;

the sleeve member has a generally elliptical cross-section, wherein when the sleeve member is within a range of pivoting around the second side, a gap through which the belt-shaped body can pass is, in a natural state, present between an outer circumferential surface of the ring attachment member and an outer circumferential surface of the sleeve member; and the sleeve member includes, in a range of the outer circumferential surface of the sleeve member that can face the first side, a first region that allows the outer cloth to slide when the region continuous with the outer circumferential end of the belt-shaped body is pulled through the ring in a direction away from the measurement site by arm strength and a second region having a projection that, when the region continuous with the outer circumferential end of the belt-shaped body attempts to return through the ring due to elastic force of the measurement site, enters into the gap as a result of the sleeve member rotating around the second side due to the belt-shaped body and catches on and applies friction to the outer cloth, in that order from an upstream side toward a downstream side with respect to a direction in which the region continuous with the outer circumferential end of the belt-shaped body is pulled.

2. The blood pressure measurement cuff according to claim 1, further comprising:

a restricting element that restricts a range in which the sleeve member can pivot around the second side to a range from a first angled position, at which the first region of the outer circumferential surface of the sleeve member opposes the first side, to a second angled position, at which the second region opposes the first side.

3. The blood pressure measurement cuff according to claim 2, wherein the restricting element includes the outer circumferential surface of the sleeve member as a first restricting element; and a radius of a cross-section of the sleeve member perpendicular to the second side increases gradually around the sleeve member with distance from a border between the first region and the second region, and when the sleeve member rotates around the second side with the region continuous with the outer circumferential end of the belt-shaped body passed through the ring, the outer circumferential surface of the sleeve member makes contact and engages with the outer cloth of the belt-shaped body passing through the ring.

4. The blood pressure measurement cuff according to claim 2, wherein when viewed along a length direction of the sleeve member, a tip of the projection in the second region projects at an angle away from the border between the first region and the second region, around the circumference of the sleeve member.

5. The blood pressure measurement cuff according to claim 3, wherein when viewed along a length direction of the sleeve member, a tip of the projection in the second region projects at an angle away from the border between the first region and the second region, around the circumference of the sleeve member.

6. The blood pressure measurement cuff according to claim 3, wherein the restricting element includes, as a second restriction element, a pin projecting from an end surface of the sleeve member in a length direction thereof and disposed in a predetermined location corresponding to the first region around the center of the sleeve member; and the pin makes contact and engages with the connecting portion of the ring when the sleeve member rotates around the second side, and as a result, the first angled position is restricted to an angled position closer to a neutral position, at which the border between the first region and the second region of the outer circumferential surface of the sleeve member opposes the first side, than an angled position determined by the outer circumferential surface of the sleeve member serving as the first restricting element.

7. The blood pressure measurement cuff according to claim 6, wherein when viewed along the length direction of the sleeve member, a tip of the projection in the second region projects at an angle away from the border between the first region and the second region, around the circumference of the sleeve member.

8. The blood pressure measurement cuff according to claim 1, wherein the projection suppresses a state in which the belt-shaped body slackens beyond a predetermined set amount.

9. The blood pressure measurement cuff according to claim 8, wherein when viewed along a length direction of the sleeve member, a tip of the projection in the second region projects at an angle away from the border between the first region and the second region, around the circumference of the sleeve member.

10. The blood pressure measurement cuff according to claim 9, wherein a plurality of the projections of the second region are provided and are arranged along the circumference of the sleeve member.

11. The blood pressure measurement cuff according to claim 1,
wherein an expanded portion extending along a length direction of the first side is provided around the first side, and the expanded portion is wrapped by the ring attachment member.

12. The blood pressure measurement cuff according to claim 11,
wherein the expanded portion is made from an elastic material.

13. The blood pressure measurement cuff according to claim 1,
wherein an indentation allowing a fluid within the fluid bladder to flow in the circumferential direction is provided on a side of the outer circumferential surface of the sleeve member around the second side that opposes the first side, in a specific location with respect to a length direction of the second side.

14. The blood pressure measurement cuff according to claim 1,
wherein the belt-shaped body has a substantially uniform thickness.

15. The blood pressure measurement cuff according to claim 1,
wherein the outer cloth of the belt-shaped body has raised fibers, and the raised fibers are down-grain with respect to the direction in which the region continuous with the outer circumferential end is pulled through the ring.

16. The blood pressure measurement cuff according to claim 1,
wherein the region of the outer circumferential end side of the belt-shaped body where the hook-and-loop fastener is provided is in a state of being passed through the ring, and the belt-shaped body has a substantially ring shape as a result.

17. The blood pressure measurement cuff according to claim 1,
wherein when viewed along a length direction of the sleeve member, a tip of the projection in the second region projects at an angle away from the border between the first region and the second region, around the circumference of the sleeve member.

18. A blood pressure measurement cuff to be wrapped in one direction along a circumferential direction around a measurement site, the blood pressure measurement cuff comprising:
a belt-shaped body obtained by enveloping a fluid bladder with an inner cloth to be in contact with the measurement site and an outer cloth opposing the inner cloth;
a ring attached via a ring attachment member to a region on an inner circumferential end side of the outer cloth; and
a hook-and-loop fastener provided in a region on an outer circumferential end side of the inner cloth and fixed detachably to the outer cloth,
wherein the ring includes a first side that extends in a direction intersecting the circumferential direction, a second side that extends along the first side, and a pair of connecting portions that connect ends of the first and second sides, and at least a portion of the first side is attached to a region on the inner circumferential end side of the outer cloth so as to be surrounded by the ring attachment member;
the ring has a temporary fastening structure that allows a region continuous with an outer circumferential end of the belt-shaped body to be pulled through the ring with arm strength away from the measurement site during attachment and suppresses a case in which a region continuous with the outer circumferential end of the belt-shaped body pulled by the arm strength is pulled back through the ring by elastic force of the measurement site;
the temporary fastening structure has a sleeve member fitted around the second side so as to be capable of pivoting,
wherein when the sleeve member is within a range of pivoting around the second side, a gap through which the belt-shaped body can pass is, in a natural state, present between an outer circumferential surface of the ring attachment member and an outer circumferential surface of the sleeve member;
the sleeve member includes, in a range of the outer circumferential surface of the sleeve member that can face the first side, a first region that allows the outer cloth to slide when the region continuous with the outer circumferential end of the belt-shaped body is pulled through the ring in a direction away from the measurement site by arm strength and a second region having a projection that, when the region continuous with the outer circumferential end of the belt-shaped body attempts to return through the ring due to elastic force of the measurement site, enters into the gap as a result of the sleeve member rotating around the second side due to the belt-shaped body and catches on and applies friction to the outer cloth, in that order from an upstream side toward a downstream side with respect to a direction in which the region continuous with the outer circumferential end of the belt-shaped body is pulled; and
wherein an indentation allowing a fluid within the fluid bladder to flow in the circumferential direction is provided on a side of the outer circumferential surface of the sleeve member around the second side that opposes the first side, in a specific location with respect to a length direction of the second side.

* * * * *